(12) United States Patent
Maw et al.

(10) Patent No.: US 6,586,439 B2
(45) Date of Patent: Jul. 1, 2003

(54) PHARMACEUTICALLY ACTIVE COMPOUNDS

(75) Inventors: Graham Nigel Maw, Sandwich (GB); David James Rawson, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/189,680

(22) Filed: Jul. 3, 2002

(65) Prior Publication Data
US 2003/0013727 A1 Jan. 16, 2003

Related U.S. Application Data

(62) Division of application No. 09/650,848, filed on Aug. 29, 2000, now Pat. No. 6,440,982.

(30) Foreign Application Priority Data

Oct. 11, 1999 (GB) .............................. 9924020

(51) Int. Cl.[7] ............ A61K 31/495; A61K 31/52; C07D 239/00; C07D 473/00; C07D 401/00
(52) U.S. Cl. ............ 514/263; 514/263.2; 514/263.22; 514/263.3; 514/252.13; 514/253.02; 544/252.12; 544/257; 544/256; 544/277; 544/360
(58) Field of Search ............ 514/263, 263.2, 514/263.22, 263.3, 252.13, 253.02, 348, 351; 544/252.12, 257, 256, 277, 360

(56) References Cited

U.S. PATENT DOCUMENTS

| | | | |
|---|---|---|---|
| 4,885,301 A | 12/1989 | Coates | |
| 5,482,941 A | 1/1996 | Terrett | |
| 5,861,404 A | 1/1999 | Niewohner et al. | |
| 5,866,571 A | 2/1999 | Niewohner et al. | |
| 6,124,303 A | 9/2000 | Pamukcu et al. | |

FOREIGN PATENT DOCUMENTS

| | | | | |
|---|---|---|---|---|
| DE | 1972785 | 7/1998 | ......... | C07D/473/30 |
| EP | 0293063 | 11/1988 | ......... | C07D/473/30 |
| EP | 0352960 | 1/1990 | ......... | C07D/473/30 |
| EP | 0463756 | 2/1992 | ......... | C07D/487/04 |
| EP | 0675124 | 4/1995 | ......... | C07D/473/30 |
| EP | 0722944 | 1/1996 | ......... | C07D/473/00 |
| EP | 0722943 | 7/1996 | | |
| WO | 9400453 | * 1/1994 | | |
| WO | WO 9400453 | 1/1994 | ......... | C07D/473/30 |
| WO | WO 9616657 | 6/1996 | ......... | A61K/31/505 |
| WO | 9954333 | 10/1999 | ......... | C07D/487/04 |

OTHER PUBLICATIONS

Dumaitre, et al., "Synthesis and Cyclic GMP Phosphodiesterase Inhibitory Activity of a Series of 6–Phenylpyrazolo [3,4–d]pyrimidones", *J. Med. Chem.*, _39 pp. 1635–1644 (1996).

* cited by examiner

*Primary Examiner*—Richard L. Raymond
*Assistant Examiner*—Sudhaker B. Patel
(74) *Attorney, Agent, or Firm*—Peter C. Richardson; Gregg C. Benson; Arlene K. Musser

(57) ABSTRACT

There is provided compounds of formula IA and of formula IB,

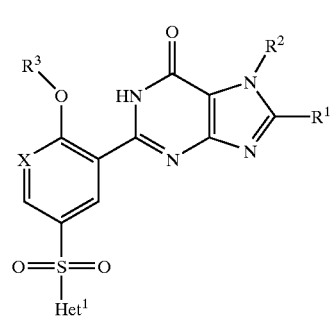

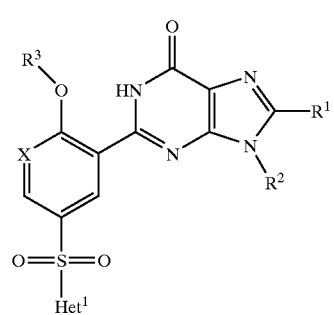

wherein $R^1$, $R^2$, $R^3$, $Het^1$ and X have meanings given in the description, which are useful in the curative and prophylactic treatment of medical conditions for which inhibition of a cyclic guanosine 3',5'-monophosphate phosphodiesterase (e.g. cGMP PDE5) is desired.

19 Claims, No Drawings

PHARMACEUTICALLY ACTIVE COMPOUNDS

This application is a divisional of U.S. patent application Ser. No. 09/650,848 filed Aug. 29, 2000, now U.S. Pat. No. 6,440,982 which claims the benefit of U.K. Provisional Patent Application No. 9924020.2 filed Oct. 11, 1999.

FIELD OF THE INVENTION

This invention relates to pharmaceutically useful compounds, in particular compounds which are useful in the inhibition of cyclic guanosine 3',5'-monophosphate phosphodiesterases (cGMP PDEs), such as type 5 cyclic guanosine 3',5'-monophosphate phosphodiesterases (cGMP PDE5). The compounds therefore have utility in a variety of therapeutic areas, including male erectile dysfunction (MED).

PRIOR ART

Certain purinone derivatives for use in inhibition of cGMP PDEs are disclosed in European patent applications EP 722943, EP 722944, EP 293063 and EP 352960, international patent applications WO 96/16657 and WO 94/00453, German patent application DE 19702785 and Japanese patent application JP 63196585. Further, EP 675124 discloses purine derivatives for use as anti-inflammatory agents.

DISCLOSURE OF THE INVENTION

According to a first aspect of the invention there is provided compounds of formulae IA and IB,

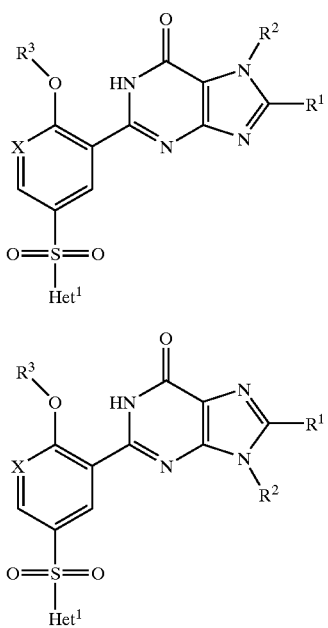

wherein
X represents CH or N;
$R^1$ represents H, —CN, —C(O)N($R^4$)$R^5$, —C(O)$R^4$, —C(O)O$R^4$, —N($R^4$)$R^6$, —O$R^7$, aryl, Het$^2$ or lower alkyl (which alkyl group is optionally interrupted by one or more of —O—, —S— or —N($R^4$)— and/or substituted and/or terminated by one or more substituents selected from halo, —CN, —NO$_2$, lower alkyl, —C(O)

N($R^4$)$R^5$, —C(O)$R^4$, —C(O)O$R^4$, —N($R^4$)$R^6$, —O$R^7$, —S(O)$_n$$R^4$—S(O)$_n$N($R^4$)$R^5$, aryl and Het$^2$);
$R^6$ represents $R^5$, —S(O)$_2$$R^8$, —S(O)$_2$N($R^4$)$R^5$, —C(O)$R^4$, —C(O)O$R^8$ or —C(O)N($R^4$)$R^5$;
$R^7$ represents $R^4$ or —C(O)$R^4$;
$R^3$, $R^4$, $R^5$ and $R^8$ independently represent, at each occurrence when used herein, lower alkyl, which alkyl group is optionally substituted and/or terminated by one or more substituents selected from lower alkyl, aryl, Het$^3$, halo, —CN, —NO$_2$, —O$R^{9a}$, —C(O)$R^{9b}$, —C(O)O$R^{9c}$, —C(O)N($R^{9d}$)$R^{9e}$, —S(O)$_2$$R^{10a}$, —S(O)$_2$N($R^{9f}$)$R^{9g}$, —OC(O)$R^{9h}$ and —N($R^{11}$)$R^{9i}$;
$R^3$, $R^4$ and $R^5$ may also, at each occurrence when used herein, independently represent H;
$R^4$, $R^5$ and $R^8$ may also, at each occurrence when used herein, independently represent aryl;
$R^2$ represents H, aryl, Het$^4$ or lower alkyl, which latter group is optionally substituted and/or terminated by one or more substituents selected from lower alkyl (which latter group is optionally substituted and/or terminated by one or more substituents selected from —OH and halo), aryl, Het$^5$, halo, —CN, —NO$_2$, —O$R^{9a}$, —C(O)$R^{9b}$, —C(O)O$R^{9c}$, —C(O)N($R^{9d}$)$R^{9e}$, —S(O)$_2$$R^{10a}$, —S(O)$_2$N($R^{9f}$)$R^{9g}$, —OC(O)$R^{9h}$ or —N($R^{11}$)$R^{9i}$;
$R^{11}$ represents, at each occurrence when used herein, H, aryl, lower alkyl (which alkyl group is optionally substituted by one or more substituents selected from aryl and halo), —C(O)$R^{9j}$, —C(O)N($R^{9k}$)$R^{9m}$ or —S(O)$_2$$R^{10b}$;
$R^{9a}$ to $R^{9m}$ independently represent, at each occurrence when used herein, H, aryl or lower alkyl (which alkyl group is optionally substituted by one or more substituents selected from aryl and halo);
$R^{10a}$ and $R^{10b}$ represent, at each occurrence when used herein, aryl or lower alkyl (which alkyl group is optionally substituted by one or more substituents selected from aryl and halo);
Het$^1$ represents an optionally substituted four- to twelve-membered heterocyclic group, which group contains at least one nitrogen atom (via which atom the Het$^1$ group is attached to the rest of the molecule) and, optionally, one or more further heteroatoms selected from nitrogen, oxygen and/or sulfur;
Het$^2$ to Het$^5$ independently represent optionally substituted four- to twelve-membered heterocyclic groups, which groups contain one or more heteroatoms selected from nitrogen, oxygen and/or sulfur;
each aryl group is optionally substituted with one or more substituents selected from halo, lower alkyl (which latter group is optionally substituted by one or more substituents selected from —CN, —NO$_2$, —O$R^{9a}$, —C(O)$R^{9b}$, —C(O)O$R^{9c}$, —C(O)N($R^{9d}$)$R^{9e}$, —S(O)$_2$N($R^{9f}$)$R^{9g}$, —S(O)$_n$$R^{10a}$, —OC(O)$R^{9h}$ and —N($R^{11}$)$R^{9i}$), —CN, —NO$_2$, —O$R^{9a}$, —C(O)$R^{9b}$, C(O)O$R^{9c}$, —C(O)N($R^{9d}$)$R^{9e}$, —S(O)$_n$$R^{10a}$, —S(O)$_2$N($R^{9f}$)$R^{9g}$, —OC(O)$R^{9h}$ and —N($R^{11}$)$R^{9i}$; Het$^1$, Het$^2$, Het$^3$, Het$^4$ and Het$^5$ are each optionally substituted with one or more substituents selected from lower alkyl (which alkyl group may itself be optionally substituted and/or terminated by one or more substituents selected from lower alkyl, aryl, Het$^2$, halo, —CN, —NO$_2$, —O$R^{9a}$, —C(O)$R^{9b}$, —C(O)O$R^{9c}$, —C(O)N($R^{9d}$)$R^{9e}$, —S(O)$_n$$R^{10a}$, —S(O)$_2$N($R^{9f}$)$R^{9g}$, —OC(O)$R^{9h}$ and —N($R^{11}$)$R^{9i}$), aryl, Het$^2$, halo, —CN, —NO$_2$, —O$R^{9a}$, —C(O)$R^{9b}$, —C(O)O$R^{9c}$, —C(O)N ($R^{9d}$)$R^{9e}$, —S(O)$_n$$R^{10a}$, (O)$_2$N($R^{9f}$)$R^{9g}$, —OC(O)$R^{9h}$ and —N($R^{11}$)$R^{9i}$; and
n represents, at each occurrence when used herein, 0, 1 or 2;
or a pharmaceutically, or a veterinarily, acceptable derivative thereof;

provided that when the compound is a compound of formula IB in which:

X represents CH;

$R^1$ represents H;

$R^3$ represents $C_{1-8}$ alkyl; and $Het^1$ represents a 5- or 6-membered saturated heterocyclic ring, which ring is optionally substituted (via a free ring N-atom) by $C_{1-6}$ alkyl (which latter group is optionally substituted by —OH);

then $R^2$ does not represent:

(a) $C_{3-11}$ alkyl, which $C_{3-11}$ alkyl group is substituted by one of the following:

(i) in the C-1 position (relative to the purinone N-atom), by —C(O)$R^{9b}$ (wherein $R^{9b}$ represents H or $C_{1-4}$ alkyl) or $C_{1-11}$ alkyl;

(ii) in the C-2 position (relative to the purinone N-atom) by one group selected from —O$R^{9a}$ (wherein $R^{9a}$ represents H, $C_{1-6}$ alkyl or benzyl), —OC(O)$R^{9h}$ (wherein $R^{9h}$ represents H, $C_{1-6}$ alkyl or phenyl) and —N($R^{11}$)$R^{9i}$ (wherein $R^{9i}$ represents H or $C_{1-6}$ alkyl and $R^{11}$ represents H, $C_{1-6}$ alkyl, —C(O)$R^{9j}$ (in which $R^{9j}$ represents H, $C_{1-6}$ alkyl or phenyl) or —S(O)$_2R^{10b}$ (in which $R^{10b}$ represents $C_{1-4}$ alkyl or phenyl)) and (optionally), at the same C-2 position, by a further $C_{1-4}$ alkyl group;

and which $C_{3-11}$ alkyl group is optionally substituted:

(I) in the C-2 to C-11 positions (relative to the purinone N-atom), by phenyl (optionally substituted by halo, —CN, —NO$_2$, $C_{1-6}$ alkyl or —S(O)$_2$N($R^{9f}$)$R^{9g}$, in which latter group $R^{9f}$ and $R^{9g}$ independently represent H, phenyl or lower alkyl); and/or (II) in the C-1 position (relative to the purinone N-atom), by $C_{1-3}$ alkyl;

(b) $C_{3-9}$ alkyl substituted in the C-2 to C-9 positions (relative to the purinone N-atom) by —N($R^{11}$)$R^{9i}$ (wherein $R^{11}$ and $R^{9i}$ each independently represent H or $C_{1-5}$ alkyl optionally substituted by phenyl, which latter group is substituted by —S(O)$_2$N($R^{9f}$)$R^{9g}$ (in which $R^{9f}$ and $R^{9g}$ independently represent H, phenyl or lower alkyl)) and optionally substituted in the C-1 position (relative to the purinone N-atom) by:

(i) $C_{1-5}$ alkyl (which alkyl group is optionally substituted by —OH); and/or (ii) $C_{1-3}$ alkyl; or (c) $C_{1-4}$ alkyl or $C_{10-16}$ n-alkyl;

wherein, in the above proviso, unless otherwise indicated, alkyl, phenyl and benzyl groups are unsubstituted, which compounds are referred to together hereinafter as "the compounds of the invention".

The term "aryl", when used herein, includes six- to ten-membered carbocyclic aromatic groups, such as phenyl and naphthyl. Unless otherwise specified, each aryl group identified herein is optionally substituted with one or more substituents selected from halo, lower alkyl (which latter group is optionally substituted by one or more substituents selected from —CN, —NO$_2$, —O$R^{9a}$, —C(O)$R^{9b}$, C(O)O$R^{9c}$, C(O)N($R^{9d}$)$R^{9e}$, —S(O)$_2$N($R^{9f}$)$R^{9g}$, —S(O)$_nR^{10a}$, —OC(O)$R^{9h}$ and —N($R^{11}$)$R^{9i}$), —CN, —NO$_2$, —O$R^{9a}$, —C(O)$R^{9b}$, —C(O)O$R^{9c}$, —C(O)N($R^{9d}$)$R^{9e}$, —S(O)$_nR^{10a}$, —S(O)$_2$N($R^{9f}$)$R^{9g}$, —OC(O)$R^{9h}$, and —N($R^{11}$)$R^{9i}$ (in which n, $R^{9a}$ to $R^{9i}$ and $R^{10a}$ are as hereinbefore defined). When aryl is substituted by a group containing one or more further aryl substituents, then such further aryl substituents may not be substituted by groups containing aryl substituents.

Het ($Het^1$, $Het^2$, $Het^3$, $Het^4$, $Het^5$) groups may be fully saturated, partly unsaturated, wholly aromatic, partly aromatic and/or bicyclic in character. Unless otherwise specified, each Het ($Het^1$, $Het^2$, $Het^3$, $Het^4$, $Het^5$) group identified herein is optionally substituted with one or more substituents selected from lower alkyl (which alkyl group may itself be optionally substituted and/or terminated as defined below in respect of $R^{12}$), aryl, $Het^2$, halo, —CN, —NO$_2$, —O$R^{9a}$, —C(O)$R^{9b}$, —C(O)O$R^{9c}$, —C(O)N($R^{9d}$)$R^{9e}$, —S(O)$_nR^{10a}$, —S(O)$_2$N($R^{9f}$)$R^{9g}$, —OC(O)$R^{9h}$, or —N($R^{11}$)$R^{9i}$ (in which n, $R^{9a}$ to $R^{9i}$, $R^{10a}$, aryl and $Het^2$ are as hereinbefore defined). Het ($Het^1$, $Het^2$, $Het^3$, $Het^4$, $Het^5$) groups that may be mentioned include groups such as optionally substituted azetidinyl, pyrrolidinyl, imidazolyl, indolyl, oxadiazolyl, thiadiazolyl, triazolyl, tetrazolyl, oxatriazolyl, thiatriazolyl, pyridazinyl, morpholinyl, pyrimidinyl, pyrazinyl, pyridyl, quinolinyl, isoquinolinyl, piperidinyl, pyrazolyl, imidazopyridinyl and piperazinyl, e.g. 4-$R^{12}$-piperazinyl, wherein $R^{12}$ represents H or lower alkyl, which latter group is optionally substituted and/or terminated by one or more substituents selected from lower alkyl, aryl, $Het^2$, halo, —CN, —NO$_2$, —O$R^{9a}$, —C(O)$R^{9b}$, —C(O)O$R^{9c}$, —C(O)N($R^{9d}$)$R^{9e}$, —S(O)$_nR^{10a}$, —S(O)$_2$N($R^{9f}$)$R^{9g}$, —OC(O)$R^{9h}$ or —N($R^{11}$)$R^{9i}$ (in which n, $R^{9a}$ to $R^{9i}$, $R^{10a}$, aryl and $Het^2$ are as hereinbefore defined). When a Het ($Het^1$, $Het^2$, $Het^3$, $Het^4$, $Het^5$) group is substituted either directly by a further $Het^2$ group or by a substituent containing a further $Het^2$ group, then such further $Het^2$ groups may not be substituted either directly by a $Het^2$ group or by a substituent containing a further $Het^2$ group.

The point of attachment of any $Het^2$, $Het^3$, $Het^4$ and $Het^5$ groups may be via any atom in the ring system including (where appropriate) a heteroatom. Het ($Het^1$, $Het^2$, $Het^3$, $Het^4$, $Het^5$) groups may also be present in the N- or S-oxidised form.

The term "lower alkyl", when used herein, includes $C_{1-12}$ alkyl, such as $C_{1-9}$ alkyl (e.g. $C_{1-6}$ alkyl). Unless otherwise specified, alkyl groups may, when there is a sufficient number of carbon atoms, be linear or branched, be saturated or unsaturated, be cyclic, acyclic or part cyclic/acyclic, be interrupted by oxygen, and/or be substituted by one or more halo atoms.

As defined herein, the term "halo" includes fluoro, chloro, bromo and iodo.

For the avoidance of doubt, each $R^4$, $R^5$, $R^8$, $R^{9a}$ to $R^{9m}$, $R^{10a}$, $R^{10b}$, $R^{11}$ and $Het^2$ group referred to herein is independent of other $R^4$, $R^5$, $R^8$, $R^{9a}$ to $R^{9m}$, $R^{10a}$, $R^{10b}$, $R^{11}$ and $Het^2$ groups, respectively. For example, when $R^2$ and $R^4$ both represent alkyl substituted by —O$R^{9a}$, the two individual —O$R^{9a}$ substituents are independent of one another, and are not necessarily identical (though this possibility is not excluded).

The pharmaceutically or veterinarily acceptable salts of the compounds of the invention which contain a basic centre are, for example, non-toxic acid addition salts formed with inorganic acids such as hydrochloric, hydrobromic, hydroiodic, sulphuric and phosphoric acid, with carboxylic acids or with organo-sulphonic acids. Examples include the HCl, HBr, HI, sulphate or bisulphate, nitrate, phosphate or hydrogen phosphate, acetate, benzoate, succinate, saccarate, fumarate, maleate, lactate, citrate, tartrate, gluconate, camsylate, methanesulphonate, ethanesulphonate, benzenesulphonate, p-toluenesulphonate and pamoate salts. Compounds of the invention can also provide pharmaceutically or veterinarily acceptable metal salts, in particular non-toxic alkali and alkaline earth metal salts, with bases. Examples include the sodium, potassium, aluminium, calcium, magnesium, zinc and diethanolamine salts. For a review on suitable pharmaceutical salts see Berge et al, J.

Pharm, Sci., 66, 1–19, 1977. Pharmaceutically acceptable derivatives also include $C_{1-4}$ alkyl ammonium salts.

The pharmaceutically acceptable solvates of the compounds of the invention include the hydrates thereof.

Also included within the scope of the compound and various salts of the invention are polymorphs thereof.

A compound of the formula (I) contains one or more asymmetric carbon atoms and therefore exists in two or more stereoisomeric forms. Where a compound of the formula (I) contains an alkenyl or alkenylene group, cis (E) and trans (Z) isomerism may also occur. The present invention includes the individual stereoisomers of the compounds of the formula (I) and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

All stereoisomers are included within the scope of the invention.

Abbreviations are listed at the end of this specification.

According to a further aspect of the invention there is provided compounds of formulae IA and IB as hereinbefore defined (but without the proviso), provided that, in the case of compounds of formula IB (or, in a still further aspect of the invention, in the case of compounds of formulae IA and/or IB), at least one of the following applies:

(1) $R^1$ represents —CN, —C(O)N($R^4$)$R^5$, —C(O)$R^4$, —C(O)O$R^4$, —N($R^4$)$R^6$, —OR$^7$, aryl, Het$^2$ or lower alkyl (which alkyl group is optionally interrupted by one or more of —O—, —S— or —N($R^4$)— and/or substituted and/or terminated by one or more substituents selected from halo, —CN, —NO$_2$, lower alkyl, —C(O)N($R^4$)$R^5$, —C(O)$R^4$, —C(O)O$R^4$, —N($R^4$)$R^6$, —OR$^7$, —S(O)$_n$$R^4$ or —S(O)$_n$N($R^4$)$R^5$, aryl and Het$^2$);

(2) $R^2$ represents H, aryl, Het$^4$, $C_{1-2}$ alkyl (which latter group is substituted by one or more substituents selected from aryl, —OR$^{9a}$, —C(O)$R^{9b}$, —OC(O)$R^{9h}$ and —N($R^{11}$)$R^{9i}$) or lower alkyl, which latter group is substituted and/or terminated by:
  (i) one or more substituents selected from halo, —CN, —NO$_2$, Het$^5$, —OR$^{9a}$, —C(O)$R^{9b}$ (wherein $R^{9a}$ and $R^{9b}$ represent aryl or lower alkyl (which alkyl group is substituted by one or more halo atoms)) —C(O)O$R^{9c}$, —C(O)N($R^{9d}$)$R^{9e}$, —S(O)$_2$$R^{10a}$, —S(O)$_2$N($R^{9f}$)$R^{9g}$ and —N($R^{11}$)$R^{9i}$ (wherein $R^{11}$ represents aryl or —C(O)N($R^{9k}$)$R^{9m}$); and/or
  (ii) more than one substituent selected from —OR$^{9a}$ (wherein $R^{9a}$ represents aryl or lower alkyl (which alkyl group is optionally substituted by one or more substituents selected from aryl and halo)), —C(O)$R^{9b}$, —OC(O)$R^{9h}$ and —N($R^{11}$)$R^{9i}$;

(3) $R^3$ represents H or lower alkyl, which alkyl group is substituted and/or terminated by one or more substituents selected from aryl, Het$^3$, halo, —CN, —NO$_2$, OR$^{9a}$ —C(O)$R^{9b}$, —C(O)O$R^{9c}$, —C(O)N($R^{9d}$)$R^{9e}$, —S(O)$_2$$R^{10a}$, —S(O)$_2$N($R^{9f}$)$R^{9g}$, —OC(O)$R^{9h}$ and —N($R^{11}$)$R^{9i}$;

(4) Het$^1$ represents:
  (i) a 4- or 7- to 12-membered optionally substituted heterocyclic group as hereinbefore defined;
  (ii) a 5- or 6-membered fully saturated heterocyclic group as hereinbefore defined, which group is not substituted by $C_{1-6}$ alkyl optionally substituted by —OH; or
  (iii) a 5- or 6-membered optionally substituted, partly unsaturated or aromatic, heterocyclic group as hereinbefore defined; and/or (5) X represents N, wherein, unless otherwise specified, substituents n, $R^4$, $R^5$, $R^6$, $R^7$, $R^{9a}$ to $R^{9m}$, $R^{10a}$, $R^{11}$, Het$^2$, Het$^4$ and Het$^5$ have meanings given in the first aspect of the invention provided hereinbefore.

Preferred compounds of the invention include those wherein:

$R^1$ represents H, —CN, —C(O)N($R^4$)$R^5$, —C(O)$R^4$, —C(O)O$R^4$, —N($R^4$)$R^6$, —OR$^7$, aryl, Het$^2$ or $C_{1-6}$ alkyl (which alkyl group is optionally substituted or terminated by one or more substituents selected from halo, —CN, —NO$_2$, lower alkyl, —C(O)N($R^4$)$R^5$, —C(O)$R^4$, —C(O)O$R^4$, —N($R^4$)$R^6$, —OR$^7$, —S(O)$_n$$R^4$, —S(O)$_n$N($R^4$)$R^5$, aryl and Het$^2$);

R represents $R^5$, —S(O)$_2$$R^8$ or —C(O)$R^4$;

$R^7$ represents $R^4$;

n represents 0 or 2;

$R^3$, $R^4$, $R^5$ and $R^8$ independently represent lower alkyl, which alkyl group is optionally substituted and/or terminated by one or more substituents selected from aryl, Het$^3$, halo, —CN, —NO$_2$, —OR$^{9a}$ or —N($R^{11}$)$R^{9i}$;

$R^3$, $R^4$ and $R^5$ may also independently represent H;

$R^4$, $R^5$ and $R^8$ may also independently represent aryl;

$R^2$ represents H, aryl, Het$^4$ or lower alkyl, which latter group is optionally substituted and/or terminated by one or more substituents selected from halo, —CN, —NO$_2$, aryl, Het$^5$, —OR$^{9a}$, —C(O)$R^{9b}$, C(O)O$R^{9c}$, —C(O)N($R^{9d}$)$R^{9e}$, —S(O)$_n$$R^{10a}$, —S(O)$_2$N($R^{9f}$)$R^{9g}$ or —N($R^{11}$)$R^{9i}$;

$R^{11}$ represents, at each occurrence, H, $C_{1-6}$ alkyl or —C(O)$R^{9i}$;

$R^{9a}$ to $R^{9j}$ independently represent, at each occurrence, H or $C_{1-6}$ alkyl;

$R^{10a}$ represents $C_{1-6}$ alkyl;

Het$^1$ represents an optionally substituted (as hereinbefore defined) four- to seven-membered heterocyclic group, which group contains at least one nitrogen atom (via which atom the Het$^1$ group is attached to the rest of the molecule) and, optionally, one or more further heteroatoms selected from nitrogen and oxygen;

Het$^2$ to Het$^5$ independently represent optionally substituted (as hereinbefore defined) four- to ten-membered heterocyclic groups, which groups contain between one and four heteroatoms selected from nitrogen, oxygen and/or sulfur.

More preferred compounds of the invention include those wherein:

$R^1$ represents H, —C(O)N($R^4$)$R^5$, —C(O)O$R^4$, —N($R^4$)$R^6$, —OR$^7$, optionally substituted phenyl, Het$^2$ or $C_{1-3}$ alkyl (which alkyl group is optionally substituted or terminated by one or more substituents selected from halo, $C_{1-3}$ alkyl, —C(O)N($R^4$)$R^5$, —C(O)O$R^4$, —N($R^4$)$R^6$, —OR$^7$, optionally substituted phenyl, and Het$^2$);

$R^6$ represents H, $C_{1-4}$ alkyl, —S(O)$_2$—($C_{1-4}$ alkyl) or —C(O)—($C_{1-14}$ alkyl);

$R^7$ represents H, or $C_{1-4}$ alkyl;

$R^3$, $R^4$, $R^5$ independently represent H or $C_{1-6}$ alkyl, which alkyl group is optionally substituted and/or terminated by one or more substituents selected from phenyl, Het$^3$, halo, —OR$^{9a}$ or —N($R^{11}$)$R^{9i}$;

$R^4$ and $R^5$ may also independently represent optionally substituted phenyl;

$R^2$ represents H, optionally substituted phenyl, Het$^4$ or $C_{1-6}$ alkyl, which latter group is optionally substituted and/or terminated by one or more substituents selected from halo, —CN, —NO$_2$, phenyl, Het$^5$, —OR$^{9a}$, —C(O)R$^{9b}$, —C(O)OR$^{9c}$, —C(O)N(R$^{9d}$)R$^{9e}$, —S(O)$_2$—(C$_{1-4}$ alkyl), —S(O)$_2$N(R$^{9f}$)R$^{9g}$, or —N(R$^{11}$)R$^{9i}$;

R$^{11}$ represents, at each occurrence, H or C$_{1-4}$ alkyl;

R$^{9a}$ to R$^{9i}$ independently represent, at each occurrence, H or C$_{1-4}$ alkyl;

Het$^1$ represents a fully saturated, optionally substituted (as hereinbefore defined) four- to six-membered heterocyclic group, which group contains at least one nitrogen atom (via which atom the Het$^1$ group is attached to the rest of the molecule) and, optionally, one or more further nitrogen atoms;

Het$^2$ to Het$^5$ independently represent four- to ten-membered heterocyclic groups, which groups contain between one and four heteroatoms selected from nitrogen, oxygen and/or sulfur, and which groups are optionally substituted by one or more substituents selected from phenyl, Het$^2$, halo, —CN, —NO$_2$, lower alkyl (which alkyl group is optionally substituted by one or more substituents selected from halo, phenyl, —OR$^{9a}$ and —N(R$^{11}$)R$^{9i}$), —OR$^{9a}$, —C(O)R$^{9b}$, —C(O)OR$^{9c}$, —C(O)N(R$^{9d}$)R$^{9e}$, —S(O)$_2$N(R$^{9f}$)R$^{9g}$ and —N(R$^{11}$)R$^{9i}$.

Still further preferred compounds of the invention include those wherein:

R$^1$ represents H, phenyl, Het$^2$ or C$_{1-2}$ alkyl (which alkyl group is optionally substituted or terminated by one or more substituents selected from halo, C$_{1-2}$ alkyl, phenyl (which phenyl group is optionally substituted by one or more substituents selected from halo, —CN, —NO$_2$, —OR$^{9a}$, —C(O)R$^{9b}$, —C(O)OR$^{9c}$, —C(O)N(R$^{9d}$)R$^{9e}$ and —N(R$^{11}$)R$^{9i}$), and Het$^2$);

R$^3$ represents C$_{1-4}$ alkyl, which alkyl group is optionally substituted and/or terminated by one or more substituents selected from phenyl, Het$^3$, halo, —OR$^{9a}$ or N(R$^{11}$R$^{9i}$;

R$^2$ represents H, phenyl (which phenyl group is optionally substituted by one or more substituents selected from halo, —CN, —NO$_2$, —OR$^{9a}$ —C(O)R$^{9b}$, —C(O)OR$^{9c}$, —C(O)N(R$^{9d}$)R$^{9e}$ and —N(R$^{11}$)R$^{9i}$) or C$_{1-4}$ alkyl (which alkyl group is optionally substituted and/or terminated by one or more substituents selected from halo, —CN, —NO$_2$, phenyl, Het$^5$, —OR$^{9a}$ or —N(R$^{11}$)R$^{9i}$);

Het$^1$ represents a fully saturated six-membered heterocyclic group, which group contains at least one nitrogen atom (via which atom the Het$^1$ group is attached to the rest of the molecule) and, optionally, one or more further nitrogen atoms, and which group is optionally substituted by one or more substituents selected from aryl, Het$^2$, halo, C$_{1-4}$ alkyl, —C(O)R$^{9b}$, and —C(O)OR$^{9c}$;

Het$^2$ represents a six-membered optionally aromatic heterocyclic group, which group contains at least one nitrogen atom and optionally one or two further heteroatoms selected from nitrogen, oxygen and/or sulfur, and which group is optionally substituted by one or more substituents selected from halo, —CN, C$_{1-4}$ alkyl, —C(O)R$^{9b}$, —C(O)OR$^{9c}$ and —N(H)R$^{11}$; R$^{9a}$ to R$^{9e}$, R$^{9i}$ and R$^{11}$ represent, at each occurrence, H or C$_{1-2}$ alkyl.

Particularly preferred compounds of the invention include those wherein:

R$^1$ represents H, —CH$_3$, -benzyl or -pyridyl;

R$^2$ represents H, phenyl (which phenyl group is optionally substituted by one or more substituents selected from —NO$_2$ and —NH$_2$) or C$_{1-3}$ alkyl;

R$^3$ represents C$_{2-4}$ alkyl;

Het$^1$ represents piperazin-1-yl, optionally substituted in the 4-position by C$_{1-2}$ alkyl or pyridyl.

Preferred compounds of the invention include the compounds of the Examples described hereinafter.

Thus, according to a further aspect of the invention, there is provided a compound of formula I which, irrespective of any of the foregoing definitions and/or provisos, is:

2-[5-(4-ethylpiperazin-1-ylsulfonyl)-2-n-propoxyphenyl]-9H-purin-6-one;

8-benzyl-2-[2-ethoxy-5-(4-ethylpiperazin-1-ylsulfonyl) phenyl]-9-n-propyl-purin-6-one;

2-[5-(4-ethylpiperazin-1-ylsulfonyl)-2-n-propoxyphenyl]-9-(4-nitrophenyl)-purin-6-one;

9-(4-aminophenyl)-2-[5-(4-ethylpiperazin-1-ylsulfonyl)-2-n-propoxy-phenyl]purin-6-one;

2-[5-(4-methylpiperazin-1-ylsulfonyl)-2-n-propoxyphenyl]-8-(pyridin-3-yl)-9H-purin-6-one;

2-[2-ethoxy-5-(4-ethylpiperazin-1-ylsulfonyl)pyridin-3-yl]-8-methyl-9-n-propylpurin-6-one;

8-benzyl-2-[2-n-butoxy-5-(4-ethylpiperazin-1-ylsulfonyl) pyridin-3-yl]-9-n-propylpurin-6-one;

2-(2-n-propoxy-5-[4-{pyridin-2-yl}piperazin-1-ylsulfonyl] phenyl)-9H-purin-6-one;

2-(2-n-propoxy-5-[4-{pyridin-2-yl}piperazin-1-ylsulfonyl] phenyl)-9-n-propylpurin-6-one;

2-[5-(4-ethylpiperazin-1-ylsulfonyl)-2-n-propoxyphenyl]-7-n-propylpurin-6-one;

2-[5-(4-ethylpiperazin-1-ylsulfonyl)-2-n-propoxyphenyl]-7-(4-nitrophenyl)-purin-6-one; or 7-(4-aminophenyl)-2-[5-(4-ethylpiperazin-1-ylsulfonyl)-2-n-propoxy-phenyl]purin-6-one;

which compounds may also be termed "compounds of the invention".

Especially preferred compounds of the invention include those wherein:

R$^1$ represents H, —CH$_3$, -benzyl or -pyridyl;

R$^2$ represents H, phenyl (which phenyl group is substituted (e.g. in position 4 relative to the point of attachment to the nitrogen atom) by one or more substituents selected from —NO$_2$ and —NH$_2$) or propyl;

R$^3$ represents C$_{2-4}$ alkyl;

Het$^1$ represents piperazin-1-yl, optionally substituted in the 4-position by C$_{1-2}$ alkyl.

The compounds of the invention may exhibit tautomerism. All tautomeric forms of the compounds of formulae IA and IB, and mixtures thereof, are included within the scope of the invention.

The compounds of the invention may also contain one or more asymmetric carbon atoms and may therefore exhibit optical and/or diastereoisomerism. Diastereoisomers may be separated using conventional techniques e.g. by fractional crystallisation or chromatography. The various stereoisomers may be isolated by separation of a racemic or other mixture of the compounds using conventional techniques e.g. fractional crystallisation or HPLC. The desired optical isomers may be prepared by reaction of the appropriate optically active starting materials under conditions which will not cause racemisation or epimerisation. Alternatively, the desired optical isomers may be prepared by resolution, either by HPLC of the racemate using a suitable chiral support or, where appropriate, by fractional crystallisation of the diastereoisomeric salts formed by reaction of the racemate with a suitable optically active acid or base. All stereoisomers are included within the scope of the invention.

Also included within the scope of the invention are radiolabelled derivatives of compounds of formulae IA and IB which are suitable for biological studies.

Preparation

According to a further aspect of the invention there is provided processes for the preparation of compounds of the invention, as illustrated below.

The following processes are illustrative of the general synthetic procedures which may be adopted in order to obtain the compounds of the invention:

1. Compounds of formulae IA and IB may be prepared by cyclisation of corresponding compounds of formulae IIA and IIB, respectively,

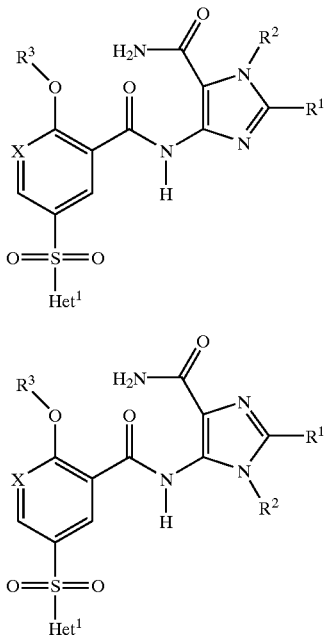

wherein $R^1$, $R^2$, $R^3$, $Het^1$ and X are as hereinbefore defined.

This cyclisation may be accomplished under basic, neutral or acidic conditions using known methods for pyrimidinone ring formation. Preferably, the cyclisation is performed under basic conditions using an alkali metal salt of an alcohol or amine, such as potassium tert-butoxide or potassium bis(trimethylsilyl) amide, in the presence of a suitable solvent (e.g. an alcohol), for example at elevated (e.g. reflux) temperature (or, if a sealed vessel is employed, at above reflux temperature). The skilled person will appreciate that, when an alcohol is selected as solvent, an appropriate alcohol of formula $R^3OH$, or a sterically hindered alcohol, e.g. 3-methyl pentan-3-ol, may be used if it is intended to mitigate alkoxide exchange at either the 2-position of the pyridin-3-yl, or the phenyl, substituent.

Compounds of formulae IIA and IIB may be prepared by reaction of corresponding compounds of formulae IIIA and IIIB, respectively,

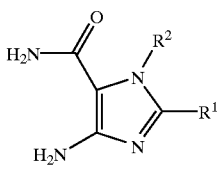

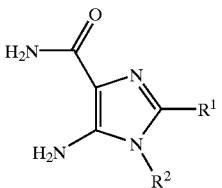

wherein $R^1$ and $R^2$ are as hereinbefore defined, with a compound of formula IV,

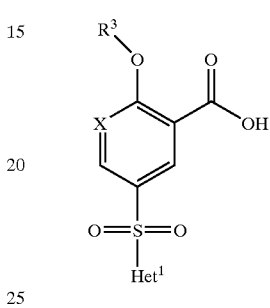

or a suitable carboxylic acid derivative thereof (e.g. an acid halide or anhydride), wherein $R^3$, $Het^1$ and X are as hereinbefore defined.

This coupling reaction may be achieved by conventional amide bond forming techniques which are well known to those skilled in the art. For example, an acid halide (e.g. chloride) derivative of a compound of formula IV may be reacted with a compound of formula IIIA or IIIB, at between −10° C. and room temperature, in the presence of an appropriate base (e.g. triethylamine, pyridine or, especially, sodium hydride) and optionally in the presence of a suitable catalyst (e.g. 4-(dimethylamino)-pyridine) and/or a suitable solvent (e.g. dichloromethane, THF or N,N-dimethylformamide).

A variety of other amino acid coupling methodologies may be used to couple a compound of formula IIIA or IIIB with a compound of formula IV. For example, the acid of formula IV or a suitable salt thereof (e.g. sodium salt) may be activated with an appropriate activating reagent (e.g. a carbodiimide, such as 1,3-dicyclohexylcarbodiimide or 1-(3-dimethyl-aminopropyl)-3-ethylcarbodiimide hydrochloride; a halotrisamino-phosphonium salt such as bromotripyrrolidinophosphonium hexafluoro-phosphate or benzotriazol-1-yloxytrispyrrolidinophosphonium hexafluoro-phosphate; or a suitable pyridinium salt such as 2-chloro-1-methyl pyridinium chloride), optionally in the presence of 1-hydroxybenzotriazole hydrate and/or a catalyst such as 4-(dimethylamino)pyridine. The coupling reaction may be conducted in a suitable solvent such as dichloromethane, N,N-dimethylformamide or tetrahydrofuran, in the presence of a suitable base (e.g. sodium hydride and, optionally, 4-methylmorpholine or N-ethyldiisopropylamine), at between −10° C. and +60° C. Preferably, from about 1 to 2 molecular eqs. of the activating reagent and from 1 to 3 molecular eqs. of any base present may be employed.

Alternatively, the carboxylic acid function of IV may be activated, at between room and reflux temperature, using an excess of a reagent such as 1,1'-carbonyldiimidazole in an appropriate solvent, e.g. ethyl acetate, dichloromethane or butan-2-one, followed by reaction of the intermediate imidazolide, at between room and reflux temperature, with a compound of formula IIIA or IIIB.

Compounds of formula IV may be prepared by standard techniques known to those skilled in the art from a corresponding halophenyl or 3-halopyridyl precursor, via hydrolysis (e.g. under basic conditions) of an intermediate alkoxycarbonyl compound, which latter compound may be obtained by reaction of the halophenyl or 3-halopyridyl compound with carbon monoxide and a lower alkyl (e.g. $C_{1-4}$) alcohol in the presence of a suitable catalyst system (e.g. tetrakis(triphenylphosphine)palladium(0)).

2. Compounds of formulae IA and IB may alternatively be prepared by reaction of corresponding compounds of formulae VA and VB, respectively,

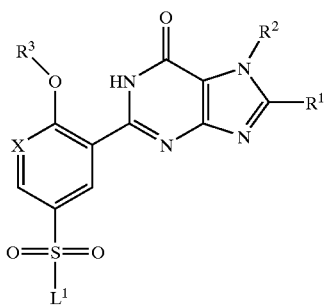

VA

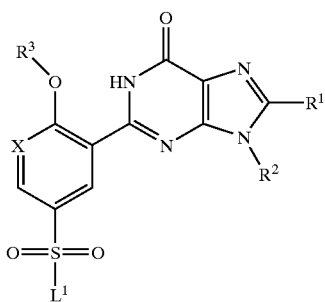

VB wherein $L^1$ is a leaving group (e.g. halo) and $R^1$, $R^2$, $R^3$ and X are as hereinbefore defined, with a compound of formula VI, Het$^1$—H         VI wherein Het$^1$ is as hereinbefore defined, provided that the essential nitrogen atom of the heterocycle is attached to the H-atom.

This reaction is typically performed at between −10° C. and room temperature in the presence of an appropriate solvent (e.g. a $C_{1-3}$ alcohol, ethyl acetate or dichloromethane), an excess of the compound of formula VI and, optionally, another suitable base (e.g. triethylamine or N-ethyldiisopropylamine).

Compounds of formula VA and VB, in which X represents N, may be prepared from corresponding compounds of formulae VIIA and VIIB, respectively,

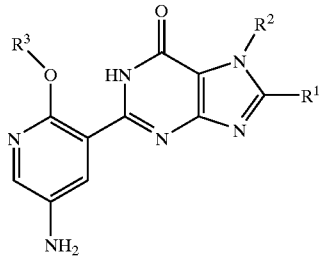

VIIA

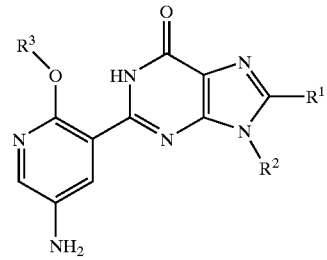

VIIB wherein $R^1$, $R^2$ and $R^3$ are as hereinbefore defined, for example using methods known to those skilled in the art for converting an amino group to an $SO_2L^1$ group, in which $L^1$ is as hereinbefore defined. For example, compounds of formulae VA and VB in which $L^1$ is chloro may be prepared by reacting a corresponding compound of formula VIIA or VIIB, at between about −25 and about 0° C., with about a 1.5 to 2-fold excess of sodium nitrite in a mixture of concentrated hydrochloric acid and glacial acetic acid, followed by treatment, at between −30° C. and room temperature, with excess liquid sulfur dioxide and a solution of about a three-fold excess of cupric chloride in aqueous acetic acid.

Compounds of formulae VIIA and VIIB may be prepared by cyclisation of corresponding compounds of formulae VIIIA and VIIIB, respectively,

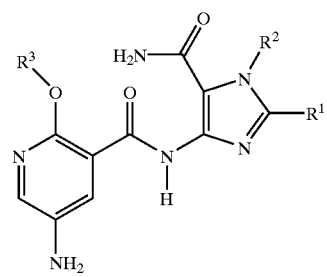

VIIIA

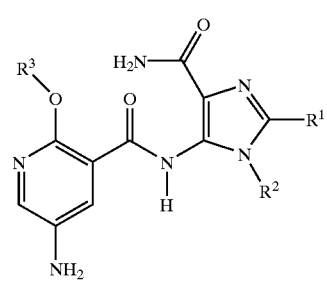

VIIIB wherein $R^1$, $R^2$ and $R^3$ are as hereinbefore defined. This cyclisation may be carried out using similar techniques to those described hereinbefore for the preparation of compounds of formulae IA and IB, but it is preferably base-mediated.

Compounds of formulae VIIIA and VIIIB may be prepared by the reduction of corresponding compounds of formulae IXA and IXB, respectively,

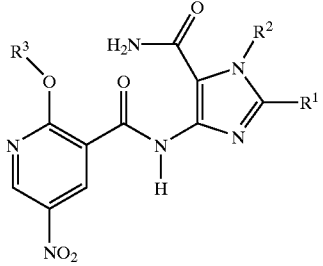

IXA

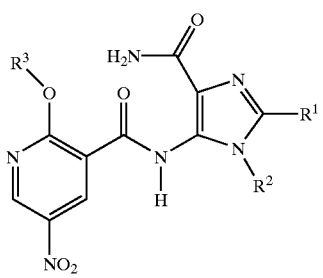

IXB wherein $R^1$, $R^2$ and $R^3$ are as hereinbefore defined, for example by conventional techniques, such as catalytic hydrogenation. Typically, the hydrogenation may be achieved at between 40 and 50° C. using a Raney® nickel catalyst in a suitable solvent (e.g. ethanol) at a hydrogen pressure of between 150 kPa and 500 kPa, especially 345 kPa.

Compounds of formulae IXA and IXB may be prepared by reaction of corresponding compounds of formulae IIIA and IIIB, as hereinbefore defined, with a compound of formula X,

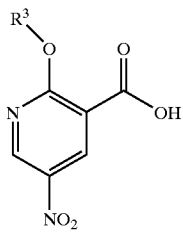

X or a suitable carboxylic acid derivative (e.g. an acid halide) thereof, wherein $R^3$ is as hereinbefore defined, for example using analogous amide bond forming techniques to those previously described for the synthesis of compounds of formulae IIA and IIB.

Compounds of formulae VIIA and VIIB may alternatively be prepared by reduction of corresponding compounds of formulae XIA and XIB, respectively:

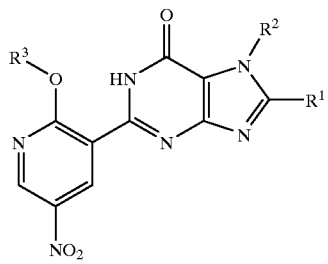

XIA

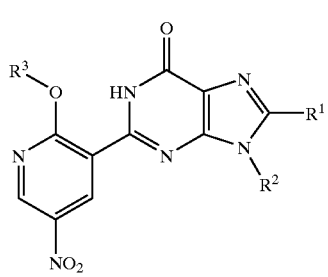

XIB wherein $R^1$, $R^2$ and $R^3$ are as hereinbefore defined. This reduction may be performed under a variety of reaction conditions, for example by catalytic hydrogenation (e.g. using 10% Pd/C in an alcohol, such as ethanol, at 415 kPa $H_2$ pressure and room temperature) or by transition metal catalysed reduction (e.g. at around room temperature in the presence of iron powder (e.g. 7 eq.) in acetic acid, or $TiCl_3$ (e.g. 9 eq.) in acetic acid).

Compounds of formulae XIA and XIB may be prepared by cyclisation of corresponding compounds of formulae IXA and IXB, respectively, for example under conditions described hereinbefore for the synthesis of compounds of formulae IA and IB.

Compounds of formulae XIA and XIB in which $R^1$ represents lower alkyl (which alkyl group is branched and unsaturated at the carbon atom that is attached to the rest of the molecule), $-N(R^4)R^5$, $-CN$, aryl or $Het^2$ (which $Het^2$ group is either aromatic, or is unsaturated at the carbon atom that is attached to the rest of the molecule) may alternatively be prepared by reaction of corresponding compounds of formulae XIVA or XIVB, respectively,

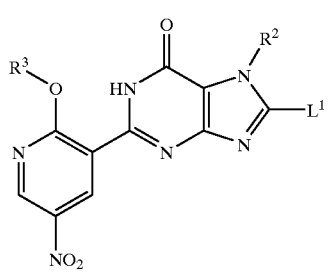

XIVA

XIVB

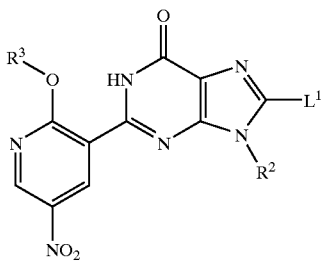

wherein $R^2$, $R^3$ and $L^1$ are as hereinbefore defined, with a compound of formula XV, $$R^{1a}M \qquad \qquad XV$$

wherein $R^{1a}$ represents lower alkyl (which alkyl group is branched and unsaturated at the carbon atom that is attached to the rest of the molecule), —N($R^4$)$R^5$, —CN, aryl or $Het^2$ (which $Het^2$ group is either aromatic, or is unsaturated at the carbon atom that is attached to M), M represents H or an optionally substituted metal or boron group, which group is suitable for cross-coupling reactions (such as a trialkylstannane (e.g. tri-n-butylstannane), a dialkylborane (e.g. diethylborane), a dialkoxyborane, a dihydroxyborane, lithium, a halomagnesium, a halozinc, copper, or a halomercury), and $R^4$ and $R^5$ are as hereinbefore defined, for example in the presence of an appropriate catalyst system (e.g. a palladium or nickel catalyst).

The cross-coupling reaction is preferably carried out in the presence of a base (e.g. potassium carbonate, cesium fluoride or triethylamine), preferably in excess. Those skilled in the art will appreciate that the type of catalyst that is employed will depend on factors such as the nature of the M group, and the substrate that is employed etc.

Suitable coupling conditions include so-called "Suzuki" conditions (e.g. 1.2 eq. of boronic acid, 2 eq. of $K_2CO_3$ and 0.1 eq. of Pd(PPh$_3$)$_4$, refluxing in an approximately 4:1 mixture of dioxane:water, or 2.5 to 3 eq. of CsF, 0.05 to 0.1 eq. of Pd$_2$(dba)$_3$ and 0.01 to 0.04 eq of P(o-tol)$_3$, refluxing in DME); or so-called "Stille" conditions (1.5 eq. of stannane, 10 eq. of LiCl, 0.15 eq. of CuI, and 0.1 eq. of Pd(PPh$_3$)$_4$, refluxing in dioxane, or 5 eq. of stannane, 3.6 eq. of Et$_3$N, Pd$_2$(dba) and P(o-tol)$_3$, refluxing in MeCN).

In a further typical procedure, a compound of formula XV may be used, in which M is halozinc. Such a compound may be prepared by reaction of a compound $R^{1a}$-halo, where halo and $R^{2a}$ are as hereinbefore defined, with an alkyllithium (e.g. n-butyllithium) at between −78° C. and room temperature in a suitable solvent (e.g. THF), and the resultant solution is then treated with Zn(II) chloride (solution in ether). The resulting mixture is then treated with a compound of formula XIVA or XIVB in the presence of a palladium catalyst (e.g. tetrakis(triphenyl)phosphine palladium(0)) in a suitable solvent (e.g. THF). The reaction may be carried out at between room and reflux temperature.

Compounds of formulae XIVA and XIVB in which $L^1$ represents halo may be prepared by halogenation of corresponding compounds of formulae XIA and XIB, respectively, in which $R^1$ represents H, under conditions known to those skilled in the art. Such conditions include, for example, in the case where $L^1$ represents bromo, reaction at between 10 and 50° C. with bromine in the presence of a suitable solvent (e.g. water or dichloromethane).

Compounds of formulae VA and VB, in which X is N, may alternatively be prepared from corresponding compounds of formulae XVIA and XVIB, respectively,

XVIA

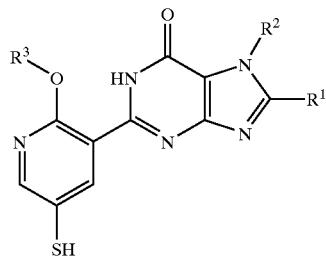

XVIB

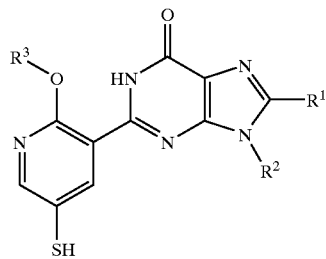

wherein $R^1$, $R^2$ and $R^3$ are as hereinbefore defined, for example by way of known reactions that will result in conversion of a thiol to an —$SO_2L^1$ group. For example, for compounds of formulae VA and VB in which $L^1$ represents halo, the reaction may be carried out at between −10° C. and reflux temperature in the presence of a suitable oxidising agent (e.g. potassium nitrate), an appropriate halogenating agent (e.g. thionyl chloride) and a suitable solvent (e.g. acetonitrile).

Compounds of formulae XVIA and XVIB may be prepared by reaction of corresponding compounds of formulae XVIIA and XVIIB, respectively,

XVIIA

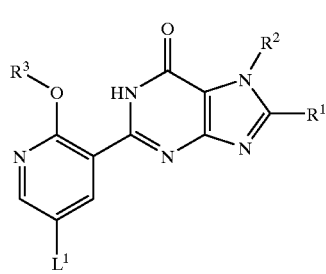

XVIIB

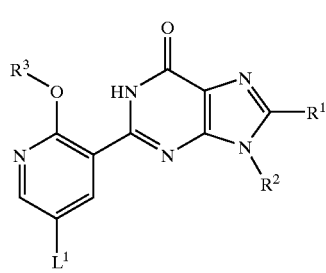

wherein $R^1$, $R^2$, $R^3$ and $L^1$ are as hereinbefore defined (and $L^1$ is preferably iodo), with a suitable sulfur-delivering reagent. For example, the reaction may be carried out at between room and reflux temperature in the presence of thiourea, an appropriate coupling catalyst (e.g. dichlorobis (triethylphosphine)nickel(II) in combination with a reducing agent such as sodium cyanoborohydride) and a suitable solvent (e.g. N,N-dimethylformamide), followed by hydrolysis in the presence of a base such as calcium oxide.

Compounds of formulae XVIIA and XVIIB may be prepared by cyclisation of corresponding compounds of formulae XVIIIA and XVIIIB, respectively,

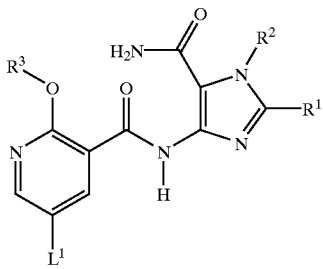

XVIIIA

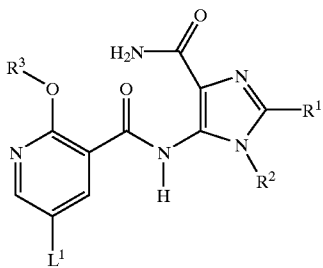

XVIIIB wherein $R^1$, $R^2$, $R^3$ and $L^1$ are as hereinbefore defined. This cyclisation may be carried out using similar techniques to those described hereinbefore for the preparation of compounds of formulae IA and IB, but it is preferably base-mediated.

Compounds of formulae XVIIIA and XVIIIB may be prepared by reaction of corresponding compounds of formulae IIIA and IIIB, respectively, as hereinbefore defined, with a compound of formula XIX,

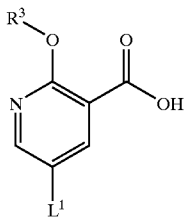

XIX or a suitable carboxylic acid derivative (e.g. an acid halide) thereof, wherein $R^3$ is as hereinbefore defined, for example using analogous amide bond forming techniques to those previously described for the synthesis of compounds of formulae IIA and IIB.

Compounds of formulae VA and VB, in which X is CH, may be prepared from corresponding compounds of formulae XXA and XXB, respectively,

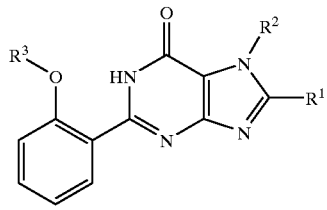

XXA

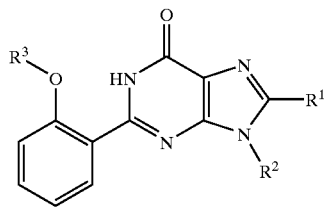

XXB wherein $R^1$, $R^2$ and $R^3$ are as hereinbefore defined, for example using conventional methods for the introduction of a $-SO_2L^1$ group into an aromatic ring system, such as reaction of a compound of formula XXA or XXB, optionally in the presence of an appropriate solvent (e.g. dichloromethane), with a compound of formula $L^1SO_3H$ and (optionally) a compound of formula $SO(L^1)_2$. When $L^1$ is chloro, reaction may take place at between 0° C. and room temperature in the presence of an excess of chlorosulfonic acid (optionally in conjunction with an excess of thionyl chloride), and optionally in an appropriate organic solvent (e.g. dichloromethane).

Compounds of formulae XXA and XXB are available using known techniques. For example, compounds of formulae XXA and XXB, in which $R^2$ represents aryl, $Het^4$ or optionally substituted lower alkyl, may be prepared by reaction of corresponding compounds of formulae XXA and XXB, respectively, in which $R^2$ represents H, with a compound of formula XXI, $$R^{2a}-L^2 \qquad \qquad XXI$$

wherein $R^{2a}$ represents aryl, $Het^4$ or lower alkyl (which latter group is optionally substituted as defined hereinbefore in respect of $R^2$ in compounds of formulae IA and IB), and $L^2$ represents a leaving group such as halo, alkane sulfonate, perfluoroalkane sulfonate or arene sulfonate, for example using methods which are known to those skilled in the art. Preferably, the leaving group is halo (preferably chloro, bromo or iodo) and the reaction is performed at between −70 and 140° C. in the presence of a suitable base (e.g. cesium carbonate, potassium hydroxide or sodium hydride), an appropriate solvent (e.g. N,N-dimethylformamide, DMSO or THF), and optionally in the presence of sodium iodide or potassium iodide. Preferably the alkylation is conducted at between room temperature and 80° C.

Those skilled in the art will appreciate that, in compounds of formula XXI in which $R^{2a}$ represents $Het^4$ or aryl, the $R^{2a}$ group may need to be activated by the presence of one or more electron-withdrawing groups for reaction with compounds of formulae XXA and XXB (in which $R^2$ represents H) to take place. Suitable electron-withdrawing groups for this purpose include nitro, formyl, acyl and alkoxycarbonyl. Such groups may be introduced and/or removed from the relevant aryl or $Het^4$ group using methods and under conditions that are known to those skilled in the art.

Compounds of formulae XXA and XXB in which $R^2$ represents optionally substituted lower alkyl may be obtained by reaction of compounds of formulae XXA and XXB, respectively, in which $R^2$ represents H, with a compound of formula XXII,

  XXII wherein $R^{2b}$ represents lower alkyl (which alkyl group is optionally substituted as defined hereinbefore in respect of $R^2$ in compounds of formulae IA and IB), for example under Mitsunobu-type conditions known to those skilled in the art.

Compounds of formulae XXA and XXB may alternatively be prepared by cyclisation of corresponding compounds of formulae XXIIIA and XXIIIB, respectively,

XXIIIA

XXIIIB

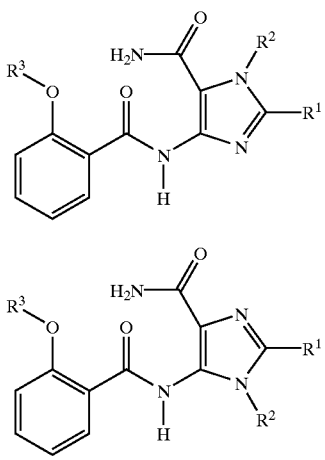

wherein $R^1$, $R^2$ and $R^3$ are as hereinbefore defined, for example under analogous conditions to those described previously for the synthesis of compounds of formulae IA and IB.

Compounds of formulae XXIIIA and XXIIIB may be prepared by reaction of corresponding compounds of formulae IIIA or IIIB, respectively, as hereinbefore defined, with a compound of formula XXIV,

XXIV

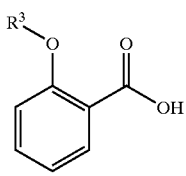

or a suitable carboxylic acid derivative (e.g. an acid halide) thereof, wherein $R^3$ is as hereinbefore defined, for example using analogous amide bond forming techniques to those previously described for the synthesis of compounds of formulae IIA and IIB.

Compounds of formulae XXIIIA and XXIIIB may alternatively be prepared by reaction of corresponding compounds of formulae XXIVA or XXIVB, respectively,

XXIVA

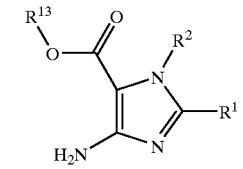

XXIVB

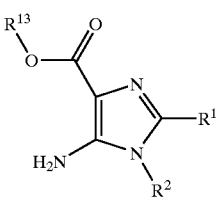

wherein $R^{13}$ represents a lower (e.g. $C_{1-6}$) alkyl group and $R^1$ and $R^2$ are as hereinbefore defined, with a compound of formula XXIV, as hereinbefore defined, followed by conversion of the $-C(O)OR^{13}$ group of the resultant amide into a $-C(O)NH_2$ group, using conventional techniques known to those skilled in the art. In a particular embodiment, the conversion of the $-C(O)OR^{13}$ group to a primary amide function and cyclisation of the resultant compound of formula XXIIIA or XXIIIB (to give a compound of formula XXA or XXB, respectively), may be accomplished in a one-pot procedure. Preferably, this one-pot procedure is accomplished with a saturated methanolic ammonia solution, in the presence of base (e.g. potassium t-butoxide), under pressure, at elevated temperatures, especially at 100° C.

Compounds of formulae XXA and XXB in which $R^2$ represents H may be prepared by reaction of a corresponding compound of formula XXV,

XXV

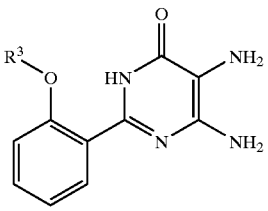

wherein $R^3$ is as hereinbefore defined, with a compound of formula XXVI, $R^1$—CHO  XXVI wherein $R^1$ is as hereinbefore defined, for example at between room and reflux temperature, optionally in the presence of a suitable mild oxidant (e.g. sodium metabisulfite), and optionally in an appropriate organic solvent (e.g. N,N-dimethyl acetamide).

Compounds of formulae XXA and XXB in which $R^2$ represents H may alternatively be prepared by reaction of a corresponding compound of formula XXV, as hereinbefore defined, with a compound of formula XXVII, $R^1$—C(O)OH  XXVII or a suitable carboxylic acid derivative thereof (e.g. an acid halide or an ortho ester), for example at between room and reflux temperature, optionally in the presence of a suitable solvent (e.g. N,N-dimethyl formamide) and/or an appropriate base.

3. Compounds of formulae IA and IB, in which $R^2$ represents aryl, $Het^4$ or optionally substituted lower alkyl, may be prepared by reaction of corresponding compounds of formulae IA and IB in which $R^2$ represents H with a compound of formula XXI, as hereinbefore defined, for example as described hereinbefore for preparation of compounds of formulae XXA and XXB.

4. Compounds of formulae IA and IB, in which $R^2$ represents optionally substituted lower alkyl, may be prepared by reaction of corresponding compounds of formulae IA and IB in which $R^2$ represents H with a compound of formula XXII, as hereinbefore defined, for example as described hereinbefore for preparation of compounds of formulae XXA and XXB.

Compounds of formulae IIIA, IIIB, VI, X, XV, XIX, XXI, XXII, XXIV, XXIVA. XXIVB, XXV, XXVI, XXVII and derivatives thereof, when not commercially available or not subsequently described, may be obtained either by analogy with the processes described hereinbefore, or by conventional synthetic procedures, in accordance with standard techniques, from readily available starting materials using appropriate reagents and reaction conditions. For example, compounds of formula XXV may be prepared by, or by analogy with, methods described in EP 352 960.

Substituents on aryl and Het ($Het^1$, $Het^2$, $Het^3$, $Het^4$, $Het^5$) groups in the above-mentioned compounds may be introduced, removed and interconverted, using techniques which are well known to those skilled in the art. For example, compounds of formulae IA and IB as described hereinbefore, in which $R^2$ represents an aminophenyl group, may be prepared by reducing corresponding compounds of formula IA or IB, in which $R^2$ represents a nitrophenyl group. The reaction may be performed using methods which are well known to those skilled in the art, for example under reduction conditions described hereinbefore.

The skilled person will also appreciate that various standard substituent or functional group interconversions and transformations within certain compounds of formulae IA and IB will provide other compounds of formulae IA and IB. For example, alkoxide exchange at the 2-position of the 5-phenyl and the pyridin-3-yl substituents. Moreover, certain compounds of formulae IA and IB, for example those in which $Het^1$ represents a 4-$R^{12}$-piperazinyl group, in which $R^{12}$ does not represent H, may be prepared directly from the corresponding piperazine analogues in which $R^{12}$ represents H, using standard procedures (e.g. alkylation).

The compounds of the invention may be isolated from their reaction mixtures using conventional techniques.

It will be appreciated by those skilled in the art that, in the course of carrying out the processes described above, the functional groups of intermediate compounds may need to be protected by protecting groups.

Functional groups which it is desirable to protect include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl and alkylcarbonyl groups (e.g. methyl- and ethylcarbonyl). Suitable protecting groups for amino include tert-butyloxycarbonyl, 9-fluorenylmethoxycarbonyl or benzyloxycarbonyl. Suitable protecting groups for carboxylic acid include $C_{1-6}$ alkyl or benzyl esters.

The protection and deprotection of functional groups may take place before or after any of the reaction steps described hereinbefore.

Protecting groups may be removed in accordance with techniques which are well known to those skilled in the art.

The use of protecting groups is fully described in "Protective Groups in Organic Chemistry", edited by J W F McOmie, Plenum Press (1973), and "Protective Groups in Organic Synthesis", $2^{nd}$ edition, T W Greene & P G M Wutz, Wiley-Interscience (1991).

Persons skilled in the art will also appreciate that, in order to obtain compounds of formula I in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

Pharmaceutically acceptable acid addition salts of the compounds of formulae IA and IB which contain a basic centre may be prepared in a conventional manner. For example, a solution of the free base may be treated with the appropriate acid, either neat or in a suitable solvent, and the resulting salt may then be isolated either by filtration or by evaporation under vacuum of the reaction solvent. Pharmaceutically acceptable base addition salts can be obtained in an analogous manner by treating a solution of a compound of formula IA or IB with the appropriate base. Both types of salt may be formed or interconverted using ion-exchange resin techniques.

The present invention also includes all suitable isotopic variations of a compound of the formula (I) or a pharmaceutically acceptable salt thereof. An isotopic variation of a compound of the formula (I) or a pharmaceutically acceptable salt thereof is defined as one in which at least one atom is replaced by an atom having the same atomic number but an atomic mass different from the atomic mass usually found in nature. Examples of isotopes that can be incorporated into compounds of the formula (I) and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$ $^{15}N$, $^{17}O$, $^{18}O$, $^{31}P$, $^{32}P$, $^{35}S$, $^{18}F$ and $^{36}Cl$, respectively. Certain isotopic variations of the compounds of the formula (I) and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the compounds of formula (I) and pharmaceutically acceptable salts thereof of this invention can generally be prepared by conventional procedures such as by the illustrative methods or by the preparations described in the Examples and Preparations hereafter using appropriate isotopic variations of suitable reagents.

It will be appreciated by those skilled in the art that certain protected derivatives of compounds of formulae IA or IB, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of formulae IA and IB may act as prodrugs of other compounds of formulae IA and IB, respectively.

All protected derivatives, and prodrugs, of compounds of formulae IA and IB are included within the scope of the invention.

The present invention additionally comprises the combination of a cGMP $PDE_5$ inhibitor, in particular a compound of the general formula (I) with:

(a) one or more naturally occurring or synthetic prostaglandins or esters thereof. Suitable prostaglandins for use herein include compounds such as alprostadil, prostaglandin $E_1$, prostaglandin $E_0$, 13, 14-dihydroprosta glandin $E_1$, prostaglandin $E_2$, eprostinol, natural synthetic and semi-synthetic prostaglandins and derivatives thereof including those described in U.S. Pat. No. 6,037,346 issued on Mar. 14, 2000 and incorporated herein by reference, $PGE_0$, $PGE_1$, $PGA_1$, $PGB_1$, $PGF_1$, $\alpha$, 19-hydroxy $PGA_1$, 19-hydroxy —$PGB_1$, $PGE_2$, $PGB_2$, 19-hydroxy-$PGA_2$, 19-hydroxy-$PGB_2$, $PGE_3\alpha$, carboprost tromethamine dinoprost, tromethamine, dinoprostone, lipo prost, gemeprost, metenoprost, sulprostune, tiaprost and moxisylate; and/or (b) one or more $\alpha$-adrenergic receptor antagonist compounds also known as $\alpha$-adrenoceptors or $\alpha$-receptors or $\alpha$-blockers. Suitable compounds for use herein include: the $\alpha$-adrenergic receptors as described in PCT application WO99/30697 published on Jun. 14, 1998, the disclosures of which relating to $\alpha$-adrenergic receptors are incorporated herein by reference and include, selective $\alpha_1$-adrenoceptors or $\alpha_2$-adrenoceptors and non-selective adrenoceptors, suitable $\alpha_1$-adrenoceptors include: phentolamine, phentolamine mesylate, trazodone, alfuzosin, indoramin, naftopidil, tamsulosin, dapiprazole, phenoxybenzamine, idazoxan, efaraxan, yohimbine, rauwolfa alkaloids, Recordati 15/2739, SNAP 1069, SNAP 5089, RS17053, SL 89.0591, doxazosin, terazosin, abanoquil and prazosin; $\alpha_2$-blockers from U.S. Pat. No. 6,037,346 [Mar. 14, 2000] dibenarnine, tolazoline, trimazosin and dibenarnine; $\alpha$-adrenergic receptors as described in U.S. Pat. Nos.: 4,188,390; 4,026,894; 3,511,836; 4,315,007; 3,527,761; 3,997,666; 2,503,059; 4,703,063; 3,381,009; 4,252,721 and 2,599,000 each of which is incorporated herein by reference; $\alpha_2$-Adrenoceptors include: clonidine, papaverine, papaverine hydrochloride, optionally in the presence of a cariotonic agent such as pirxamine; and/or (c) one or more NO-donor (NO-agonist) compounds. Suitable NO-donor compounds for use herein include organic nitrates, such as mono- di or tri-nitrates or organic nitrate esters including glyceryl brinitrate (also known as nitroglycerin), isosorbide 5-mononitrate, isosorbide dinitrate, pentaerythritol tetranitrate, erythrityl tetranitrate, sodium nitroprusside (SNP), 3-morpholinosydnonimine molsidomine, S-nitroso-N-acetyl penicilliamine (SNAP) S-nitroso-N-glutathione (SNO-GLU), N-hydroxy-L-arginine, amylnitrate, linsidomine, linsidomine chlorohydrate, (SIN-1) S-nitroso-N-cysteine, diazenium diolates, (NONOates), 1,5-pentanedinitrate, L-arginene, ginseng, zizphi fructus, molsidomine, Re-2047, nitrosylated maxisylyte derivatives such as NMI-678-11 and NMI-937 as described in published PCT application WO 0012075; and/or (d) one or more potassium channel openers. Suitable potassium channel openers for use herein include nicorandil, cromokalim, levcromakalim, lemakalim, pinacidil, cliazoxide, minoxidil, charybdotoxin, glyburide, 4-amini pyridine, $BaCl_2$; and/or (e) one or more dopaminergic agents. Suitable dopaminergic compounds for use herein include $D_2$-agonists such as, pramipexol; apomorphine; and/or (f) one or more vasodilator agents. Suitable vasodilator agents for use herein include nimodepine, pinacidil, cyclandelate, isoxsuprine, chloroprumazine, halo peridol, Rec 15/2739, trazodone, pentoxifylline; and/or (g) one or more thromboxane A2 agonists; and/or (h) one or more CNS active agents; and/or (i) one or more ergot alkoloids; Suitable ergot alkaloids are described in U.S. Pat. No. 6,037,346 issued on Mar. 14, 2000 and include acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride; and/or (k) one or more compounds which modulate the action of atrial natruretic factor (also known as atrial naturetic peptide), such as inhibitors or neutral endopeptidase; and/or (l) one or more compounds which inhibit angiotensin-converting enzyme such as enapril, and combined inhibitors of angiotensin-converting enzyme and neutral endopeptidase such as omapatrilat; and/or (m) one or more angiotensin receptor antagonists such as losartan; and/or (n) one or more substrates for NO-synthase, such as L-arginine; and/or (o) one or more calcium channel blockers such as amlodipine; and/or (p) one or more antagonists of endothelin receptors and inhibitors or endothelin-converting enzyme; and/or (q) one or more cholesterol lowering agents such as statins and fibrates; and/or (r) one or more antiplatelet and antithrombotic agents, e.g. tPA, uPA, warfarin, hirudin and other thrombin inhibitors, heparin, thromboplastin activating factor inhibitors; and/or (s) one or more insulin sensitising agents such as rezulin and hypoglycaemic agents such as glipizide; and/or (t) L-DOPA or carbidopa; and/or (u) one or more acetylcholinesterase inhibitors such as donezipil; and/or (v) one or more steroidal or non-steroidal anti-inflammatory agents.

Medical Use

The compounds of the invention are useful because they possess pharmacological activity in animals, especially mammals, including humans. They are therefore indicated as pharmaceuticals, as well as for use as animal medicaments.

According to a further aspect of the invention there is provided the compounds of the invention for use as pharmaceuticals, and for use as animal medicaments.

In particular, compounds of the invention have been found to be potent and selective inhibitors of cGMP PDEs, such as cGMP PDE5, for example as demonstrated in the tests described below, and are thus useful in the treatment of medical conditions in humans, and in animals, in which cGMP PDEs, such as cGMP PDE5, are indicated, and in which inhibition of cGMP PDEs, such as cGMP PDE5, is desirable.

By the term "treatment", we include both therapeutic (curative), palliative or prophylactic treatment.

Thus, according to a further aspect of the invention there is provided the use of the compounds of the invention in the manufacture of a medicament for the treatment of a medical condition in which a cGMP PDE (e.g. cGMP PDE5) is indicated. There is further provided the use of the compounds of the invention in the manufacture of a medicament for the treatment of a medical condition in which inhibition of a cGMP PDE (e.g. cGMP PDE5) is desirable.

The compounds of the invention are thus expected to be useful for the curative, palliative or prophylactic treatment of mammalian sexual disorders. In particular, the compounds are of value in the treatment of mammalian sexual dysfunctions such as male erectile dysfunction (MED), impotence, female sexual dysfunction (FSD), clitoral dysfunction, female hypoactive sexual desire disorder, female sexual arousal disorder, female sexual pain disorder or female sexual orgasmic dysfunction (FSOD) as well as sexual dysfunction due to spinal cord injury but, clearly, will be useful also for treating other medical conditions for which a potent and selective cGMP PDE5 inhibitor is indicated. Such conditions include premature labour, dysmenorrhoea, benign prostatic hyperplasia (BPH), bladder outlet obstruction, incontinence, stable, unstable and variant (Prinzmetal) angina, hypertension, pulmonary hypertension, chronic obstructive pulmonary disease, coronary artery disease, congestive heart failure, atherosclerosis, conditions of reduced blood vessel patency, e.g. post-percutaneous transluminal coronary angioplasty (post-PTCA), peripheral vascular disease, stroke, nitrate induced tolerance, bronchitis, allergic asthma, chronic asthma, allergic rhinitis, glaucoma and diseases characterised by disorders of gut motility, e.g. irritable bowel syndrome (IBS).

Further medical conditions for which a potent and selective cGMP PDE5 inhibitor is indicated, and for which treatment with compounds of the present invention may be useful include pre-eclampsia, Kawasaki's syndrome, nitrate tolerance, multiple sclerosis, diabetic nephropathy, peripheral diabetic neuropathy, Alzheimer's disease, acute respiratory failure, psoriasis, skin necrosis, cancer, metastasis, baldness, nutcracker oesophagus, anal fissure, haemorrhoids and hypoxic vasoconstriction.

Particularly preferred conditions include MED and FSD.

Thus the invention provides a method of treating or preventing a medical condition for which a cGMP PDE5 inhibitor is indicated, in an animal (e.g. a mammal, including a human being), which comprises administering a therapeutically effective amount of a compound of the invention to a mammal in need of such treatment.

Pharmaceutical Preparations

The compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

The compounds of the invention may also be combined with any other drugs useful in the inhibition of cGMP-PDEs, such as cGMP-PDE5.

The compounds of formulae (IA) or (1B), their pharmaceutically acceptable salts, and pharmaceutically acceptable solvates of either entity can be administered alone but, in human therapy will generally be administered in admixture with a suitable pharmaceutical excipient diluent or carrier selected with regard to the intended route of administration and standard pharmaceutical practice.

For example, the compounds of formulae (IA) or (1B) or salts or solvates thereof can be administered orally, buccally or sublingually in the form of tablets, capsules (including soft gel capsules), ovules, elixirs, solutions or suspensions, which may contain flavouring or colouring agents, for immediate-, delayed-, modified-, sustained-, controlled-release or pulsatile delivery applications. The compounds of the invention may also be administered via intracavernosal injection. The compounds of the invention may also be administered via fast dispersing or fast dissolving dosages forms.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the formula (IA) or (IB) may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients maybe present both within the dosage form i.e. within the matrix, and/or on the dosage form i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol.

The compounds of the invention can also be administered parenterally, for example, intracavernosally, intravenously, intra-arterially, intraperitoneally, intrathecally, intraventricularly, intraurethrally intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of formula (IA) or (1 B) or salts or solvates thereof will usually be from 10 to 500 mg (in single or divided doses).

Thus, for example, tablets or capsules of the compounds of formulae (IA) or (IB) or salts or solvates thereof may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will also appreciate that, in the treatment of certain conditions (including MED and FSD), compounds of the invention may be taken as a single dose on an "as required" basis (i.e. as needed or desired).

EXAMPLE TABLET FORMULATION

In general a tablet formulation could typically contain between about 0.01 mg and 500 mg of a compound according to the present invention (or a salt thereof whilst tablet fill weights may range from 50 mg to 1000 mg. An example formulation for a 10 mg tablet is illustrated;

| Ingredient | % w/w |
|---|---|
| Compound of Example 7 | 10.000* |
| Lactose | 64.125 |
| Starch | 21.375 |
| Croscarmellose Sodium | 3.000 |
| Magnesium Stearate | 1.500 |

*This quantity is typically adjusted in accordance with drug activity.

The compounds of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark] or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the formula (IA) or (IB) and a suitable powder base such as lactose or starch.

Aerosol or dry powder formulations are preferably arranged so that each metered dose or "puff" contains from 1 to 50 mg of a compound of the formula (IA) or (IB) for delivery to the patient. The overall daily dose with an aerosol will be in the range of from 1 to 50 mg which may be administered in a single dose or, more usually, in divided doses throughout the day.

The compounds of the invention may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the compounds of the formulae (IA) or (IB) or salts or solvates thereof can be administered in the form of a suppository or pessary, or they may be applied topically in the form of a gel, hydrogel, lotion, solution, cream, ointment or dusting powder. The compounds of the formulae (IA) and (IB) or salts or solvates thereof may also be dermally administered. The compounds of the formulae (IA) or (IB) or salts or solvates thereof may also be transdermally administered, for example, by the use of a skin patch. They may also be administered by the ocular, pulmonary or rectal routes.

For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the formulae (IA) or (IB) or salts or solvates thereof can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the formula (IA) or (IB) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

Generally, in humans, oral administration of the compounds of the invention is the preferred route, being the most convenient and, for example in MED, avoiding the well-known disadvantages associated with intracavernosal (i.c.) administration. A preferred oral dosing regimen in MED for a typical man is from 25 to 250 mg of compound when required. In circumstances where the recipient suffers from a swallowing disorder or from impairment of drug absorption after oral administration, the drug may be administered parenterally, sublingually or buccally.

For veterinary use, a compound of formula (IA) or (IB), or a veterinarily acceptable salt thereof, or a veterinarily acceptable solvate or pro-drug thereof, is administered as a suitably acceptable formulation in accordance with normal veterinary practice and the veterinary surgeon will determine the dosing regimen and route of administration which will be most appropriate for a particular animal.

Thus, according to a further aspect of the invention there is provided a pharmaceutical formulation including a compound of the invention in admixture with a pharmaceutically or veterinarily acceptable adjuvant, diluent or carrier.

In addition to the fact that compounds of the invention inhibit cyclic guanosine 3',5'-monophosphate phosphodiesterases (cGMP PDEs) and in particular, are potent and selective inhibitors of cGMP PDE5, compounds of the invention may also have the advantage that they may be more efficacious than, be less toxic than, have a broader range of activity than, be more potent than, produce fewer side effects than, be more easily absorbed than, or they may have other useful pharmacological properties over, compounds known in the prior art.

The biological activities of the compounds of the present invention were determined by the following test methods.
Biological Tests
Phosphodiesterase (PDE) Inhibitory Activity In vitro PDE inhibitory activities against cyclic guanosine 3',5'-monophosphate (cGMP) and cyclic adenosine 3',5'-monophosphate (cAMP) phosphodiesterases were determined by measurement of their $IC_{50}$ values (the concentration of compound required for 50% inhibition of enzyme activity).

The required PDE enzymes were isolated from a variety of sources, including human corpus cavernosum, human and rabbit platelets, human cardiac ventricle, human skeletal muscle and bovine retina, essentially by the method of W. J. Thompson and M. M. Appleman (Biochem., 1971, 10, 311). In particular, the cGMP-specific PDE (PDE5) and the cGMP-inhibited cAMP PDE (PDE3) were obtained from human corpus cavernosum tissue, human platelets or rabbit platelets; the cGMP-stimulated PDE (PDE2) was obtained from human corpus cavernosum; the calcium/calmodulin (Ca/CAM)-dependent PDE (PDE1) from human cardiac ventricle; the cAMP-specific PDE (PDE4) from human skeletal muscle; and the photoreceptor PDE (PDE6) from bovine retina. Phosphodiesterases 7–11 were generated from full length human recombinant clones transfected into SF9 cells.

Assays were performed either using a modification of the "batch" method of W. J. Thompson et al. (Biochem., 1979, 18, 5228) or using a scintillation proximity assay for the direct detection of AMP/GMP using a modification of the protocol described by Amersham plc under product code TRKQ7090/7100. In summary, the effect of PDE inhibitors was investigated by assaying a fixed amount of enzyme in the presence of varying inhibitor concentrations and low substrate, (cGMP or cAMP in a 3:1 ratio unlabelled to [$^3$H]-labeled at a conc ~1/3 Km) such that $IC_{50} \cong K_i$. The final assay volume was made up to 100 μl with assay buffer [20 mM Tris-HCl pH 7.4, 5 mM $MgCl_2$, 1 mg/ml bovine serum albumin]. Reactions were initiated with enzyme, incubated for 30–60 min at 30° C. to give <30% substrate turnover and terminated with 50 μl yttrium silicate SPA beads (containing 3 mM of the respective unlabelled cyclic nucleotide for PDEs 9 and 11). Plates were re-sealed and shaken for 20 min, after which the beads were allowed to settle for 30 min in the dark and then counted on a TopCount plate reader (Packard, Meriden, Conn.) Radioactivity units were converted to % activity of an uninhibited control (100%), plotted against inhibitor concentration and inhibitor $IC_{50}$ values obtained using the 'Fit Curve' Microsoft Excel extension. Results from these tests show that the compounds of the present invention are potent and selective inhibitors of cGMP-specific PDE5.
Functional Activity This was assessed in vitro by determining the capacity of a compound of the invention to enhance sodium nitroprusside-induced relaxation of pre-contracted rabbit corpus cavernosum tissue strips, as described by S. A. Ballard et al. (Brit. J. Pharmacol., 1996, 118 (suppl.), abstract 153P).
In vivo Activity Compounds were screened in anaesthetised dogs to determine their capacity, after i.v. administration, to enhance the pressure rises in the corpora cavernosa of the penis induced by intracavernosal injection of sodium nitroprusside, using a method based on that described by Trigo-Rocha et al. (Neurourol. and Urodyn., 1994, 13, 71).
Safety Profile Compounds of the invention may be tested at varying i.v and p.o. doses in animals such as mouse and dog, observing for any untoward effects.

EXAMPLES AND PREPARATIONS

The invention is illustrated by the following Preparations and Examples.

$^1$H nuclear magnetic resonance (NMR) spectra were recorded using either a Varian Unity 300 or a Varian Inova 400 spectrometer and were in all cases consistent with the proposed structures. Characteristic chemical shifts (δ) are given in parts-per-million downfield from tetramethylsilane.

Mass spectra (m/z) were recorded using a low resolution mass spectrometer.

Room temperature includes 20 to 25° C.
Synthesis of Intermediates
Preparation 1
5-Amino-2-methyl-1-n-propylimidazole-4-carboxamide A mixture of 2-amino-2-cyanoacetamide (prepared as described in WO 94/00453; 3.6 g, 36.4 mmol) and ethyl acetimidate hydrochloride (4.50 g, 36.4 mmol) in acetonitrile (85 mL) was stirred at 50° C. for an hour, then cooled to 0° C., and stirred for a further hour. The reaction mixture was filtered, and n-propylamine (3.02 mL, 36.4 mmol) added. The solution was stirred at room temperature for an hour, and left to stand for a further 16 hours. The resulting precipitate was filtered, washed with acetonitrile, then dichloromethane and dried under vacuum to afford the title compound as a solid (3.0 g, 45%).

δ (DMSO-$d_6$, 300 MHz): 0.85 (3H, t), 1.58 (2H, m), 2.17 (3H, s), 3.68 (2H, t), 5.66 (2H, s), 6.50 (2H, br s).
Preparation 2
5-Amino-2-benzyl-1-n-propylimidazole-4-carboxamide A solution of 2-amino-2-cyanoacetamide (prepared as described in WO 94/00453; 250 mg, 2.5 mmol) in acetonitrile (6 mL) was added to ethyl 2-phenylethanimidoate hydrochloride (prepared as described in J. Med. Chem. 38 (18), 3676 (1995); 500 mg, 2.5 mmol), and the suspension stirred at room temperature for an hour, then cooled in an ice-bath. The resulting precipitate was filtered off, n-propylamine (160 μL, 2.5 mmol) added to the filtrate and the solution stirred at room temperature for 72 hours. The reaction mixture was concentrated under reduced pressure, and the residue purified by column chromatography on silica gel using dichloromethane:methanol (95:5) as eluant to afford the title compound as a tan coloured solid (136 mg, 21%).

δ (DMSO-d$_6$, 400 MHz): 0.68 (3H, t), 1.24 (2H, m), 3.55 (2H, t), 3.92 (2H, s), 5.70 (2H, s), 7.14–7.28 (5H, m).

Preparation 3

2-Benzyl-5-(2-ethoxybenzamido)-1-n-propylimidazole-4-carboxamide (i) Oxalyl chloride (0.28 mL, 3.21 mmol) was added to an ice-cooled solution of 2-ethoxybenzoic acid (130 mg, 0.78 mmol) in dichloromethane (5 mL), followed by N,N-dimethylformamide (1 drop), and the reaction stirred at room temperature for 2 hours. The solution was concentrated under reduced pressure, azeotroped with dichloromethane and the residue redissolved in tetrahydrofuran (5 mL).

(ii) Sodium hydride (48 mg, 60% dispersion in mineral oil, 1.2 mmol) was added to a solution of 5-amino-2-benzyl-1-n-propylimidazole-4-carboxamide (Preparation 2; 200 mg, 0.77 mmol) in tetrahydrofuran (5 mL), and the mixture stirred for 3 hours at room temperature. The prepared solution of acid chloride (from (i) above) was then added and the reaction stirred at room temperature for 2 days. The mixture was concentrated under reduced pressure, the residue partitioned between dichloromethane and water, and the layers separated. The organic phase was dried (MgSO$_4$) and evaporated under reduced pressure. The crude product was purified by column chromatography on silica gel twice, using an elution gradient of dichloromethane: methanol (100:0 to 95:5) to afford the title compound (114 mg, 36%).

δ (CDCl$_3$, 300 MHz): 0.74 (3H, t), 1.42–1.60 (5H, m), 3.88 (2H, t), 4.12 (2H, s), 4.36 (2H, q), 5.30 (1H, br s), 6.86 (1H, br s), 7.03 (2H, m), 7.20–7.37 (5H, m), 7.50 (1H, m), 8.20 (1H, m), 10.42 (1H, s).

LRMS: m/z 407 (M+1)$^+$.

Preparation 4

2-n-Butoxypyridine-3-carboxylic Acid

Sodium (3.0 g, 130 mmol) was added to n-butanol (100 mL), and the mixture warmed to 80° C. until a solution was obtained, and then 2-chloro-nicotinic acid (10.0 g, 63.4 mmol) added, and the reaction heated under reflux for 4 hours. The cooled mixture (which solidified on cooling) was crushed and then partitioned between ethyl acetate and aqueous hydrochloric acid (sufficient to achieve pH 4), and the layers separated. The organic phase was washed with brine, and evaporated under reduced pressure. The residue was redissolved in ethyl acetate, dried (MgSO$_4$) and re-evaporated to give the title compound as a solid (11.9 g, 96%).

LRMS: m/z 196 (M+1)$^+$.

Preparation 5

2-n-Butoxy-5-iodopyridine-3-carboxylic Acid

N-Iodosuccinimide (6.0 g, 26.7 mmol) was added to a solution of 2-n-butoxypyridine-3-carboxylic acid (Preparation 4; 3.46 g, 17.7 mmol) in trifluoroacetic acid (28 mL) and trifluoroacetic anhydride (7 mL) and the reaction heated under reflux in the absence of light, for 3 hours. The cooled reaction mixture was concentrated under reduced pressure and the residue dissolved in ethyl acetate. This solution was washed sequentially with water (2×), aqueous sodium thiosulfate solution, aqueous sodium citrate solution, 2 N hydrochloric acid, and brine, then dried (MgSO$_4$) and evaporated under reduced pressure. The solid was triturated with pentane, filtered, washed with additional pentane and dried, to give the title compound as a white solid (3.86 g, 68%).

Anal. Found: C, 37.10; H, 3.70; N, 4.21. C$_{10}$H$_{12}$INO$_3$ requires C, 37.40; H, 3.76; N, 4.36%.

δ (CDCl$_3$, 400 MHz): 1.00 (3H, t), 1.50 (2H, m), 1.85 (2H, m), 4.59 (2H, t), 8.55 (1H, s), 8.70 (1H, s).

Preparation 6

Pyridine-2-amino-5-sulfonic Acid

2-Aminopyridine (80 g, 0.85 mol) was added portionwise over 30 minutes to oleum (320 g) and the resulting solution heated at 140° C. for 4 hours. On cooling, the reaction was poured onto ice (200 g) and the mixture stirred in an ice/salt bath for a further 2 hours. The resulting suspension was filtered, the solid washed with ice water (200 mL) and cold IMS (200 mL) and dried under suction to afford the title compound as a solid (111.3 g, 75%).

LRMS: m/z 175 (M+1)$^+$.

Preparation 7

Pyridine-2-amino-3-bromo-5-sulfonic Acid

Bromine (99 g, 0.62 mol) was added dropwise over an hour, to a hot solution of pyridine-2-amino-5-sulfonic acid (Preparation 6; 108 g, 0.62 mol) in water (600 mL) so as to maintain a steady reflux. Once the addition was complete the reaction was cooled and the resulting mixture filtered. The solid was washed with water and dried under suction to afford the title compound (53.4 g, 34%).

δ (DMSO-d$_6$, 300 MHz): 8.08 (1H, s), 8.14 (1H, s).

LRMS: m/z 253 (M)$^+$.

Preparation 8

Pyridine-3-bromo-2-chloro-5-sulfonyl Chloride

A solution of sodium nitrite (7.6 g, 110.0 mmol) in water (30 mL) was added dropwise to an ice-cooled solution of pyridine-2-amino-3-bromo-5-sulfonic acid (Preparation 7; 25.3 g, 100.0 mmol) in aqueous hydrochloric acid (115 mL, 20%), so as to maintain the temperature below 6° C. The reaction was stirred for 30 minutes at 0° C. and for a further hour at room temperature. The reaction mixture was evaporated under reduced pressure and the residue dried under vacuum at 70° C. for 72 hours. A mixture of this solid, phosphorus pentachloride (30.0 g, 144.0 mmol) and phosphorus oxychloride (1 mL, 10.8 mmol) was heated at 125° C. for 3 hours, and then cooled. The reaction mixture was poured onto ice (100 g) and the resulting solid filtered, and washed with water. The product was dissolved in dichloromethane, dried (MgSO$_4$), and evaporated under reduced pressure to afford the title compound as a yellow solid (26.58 g, 91%).

δ (CDCl$_3$, 300 MHz): 8.46 (1H, s), 8.92 (1H, s). Preparation 9

3-Bromo-2-chloro-5-(4-ethylpiperazin-1-ylsulfonyl)pyridine

A solution of 1-ethylpiperazine (11.3 mL, 89.0 mmol) and triethylamine (12.5 mL, 89.0 mmol) in dichloromethane (150 mL) was added dropwise to an ice-cooled solution of pyridine-3-bromo-2-chloro-5-sulfonyl chloride (Preparation 8; 23.0 g, 79.0 mmol) in dichloromethane (150 mL) and the reaction stirred at 0° C. for an hour. The reaction mixture was concentrated under reduced pressure and the residual brown oil was purified by column chromatography on silica gel, using an elution gradient of dichloromethane:methanol (99:1 to 97:3) to afford the title compound as an orange solid (14.5 g, 50%).

δ (CDCl$_3$, 300 MHz): 1.05 (3H, t), 2.42 (2H, q), 2.55 (4H, m), 3.12 (4H, m), 8.24 (1H, s), 8.67 (1H, s).

Preparation 10

3-Bromo-2-ethoxy-5-(4-ethylpiperazin-1-ylsulfonyl)pyridine

A mixture of 3-bromo-2-chloro-5-(4-ethylpiperazin-1-ylsulfonyl)pyridine (Preparation 9; 6.60 g, 17.9 mmol) and sodium ethoxide (6.09 g, 89.55 mmol) in ethanol (100 mL) was heated under reflux for 18 hours, then cooled. The reaction mixture was concentrated under reduced pressure, the residue partitioned between water (100 mL) and ethyl acetate (100 mL), and the layers separated. The aqueous phase was extracted with ethyl acetate (2×100 mL), the combined organic solutions dried (MgSO$_4$) and evaporated under reduced pressure to afford the title compound as a brown solid (6.41 g, 95%).

Anal. Found: C, 41.27; H, 5.33; N, 11.11. C$_{13}$H$_{20}$BrN$_3$O$_3$S requires C, 41.35; H, 5.28; N, 10.99%.

δ (CDCl$_3$, 300 MHz): 1.06 (3H, t), 1.48 (3H, t), 2.42 (2H, q), 2.56 (4H, m), 3.09 (4H, m), 4.54 (2H, q), 8.10 (1H, s), 8.46 (1H, s).

LRMS: m/z 378, 380 (M+1)$^+$.

Preparation 11
Pyridine 2-ethoxy-5-(4-ethylpiperazin-1-ylsulfonyl)-3-carboxylic Acid Ethyl Ester A mixture of 3-bromo-2-ethoxy-5-(4-ethylpiperazin-1-ylsulfonyl)pyridine (Preparation 10; 6.40 g, 16.92 mmol), triethylamine (12 mL, 86.1 mmol), and palladium(0) tetrakis (triphenylphosphine) (1.95 g, 1.69 mmol) in ethanol (60 mL) was heated at 100° C. and 1379 kPa (200 psi), under a carbon monoxide atmosphere, for 18 hours, then cooled. The reaction mixture was evaporated under reduced pressure and the residue purified by column chromatography on silica gel, using an elution gradient of dichloromethane: methanol (100:0 to 97:3) to afford the title compound as an orange oil (6.2 g, 98%).

δ (CDCl$_3$, 300 MHz): 1.02 (3H, t), 1.39 (3H, t), 1.45 (3H, t), 2.40 (2H, q), 2.54 (4H, m), 3.08 (4H, m), 4.38 (2H, q), 4.55 (2H, q), 8.37 (1H, s), 8.62 (1H, s).

LRMS: m/z 372 (M+1)$^+$.

Preparation 12
Pyridine 2-ethoxy-5-(4-ethylpiperazin-1-ylsulfonyl)-3-carboxylic Acid A mixture of pyridine 2-ethoxy-5-(4-ethylpiperazin-1-ylsulfonyl)-3-carboxylic acid ethyl ester (Preparation 11; 4.96 g, 13.35 mmol) and aqueous sodium hydroxide solution (25 mL, 2 N, 50.0 mmol) in ethanol (25 mL) was stirred at room temperature for 2 hours. The reaction mixture was concentrated under reduced pressure to half of its original volume, washed with ether and then acidified to pH 5 using 4 N hydrochloric acid. The aqueous solution was extracted with dichloromethane (3×30 mL), which organic extracts were combined, dried (MgSO$_4$) and then evaporated under reduced pressure to afford the title compound as a tan-coloured solid (4.02 g, 88%).

δ (DMSO-d$_6$, 300 MHz): 1.18 (3H, t), 1.37 (3H, t), 3.08 (2H, q), 3.17–3.35 (8H, m), 4.52 (2H, q), 8.30 (1H, s), 8.70 (1H, s).

Preparation 13
2-Benzyl-5-(2-n-butoxy-5-iodopyridin-3-ylcarboxamido)-1-n-propyl-imidazole-4-carboxamide The title compound was obtained in 40% yield from 5-amino-2-benzyl-1-n-propylimidazole-4-carboxamide (Preparation 2) and 2-n-butoxy-5-iodopyridine-3-carboxylic acid (Preparation 5), following the procedure described in Preparation 3.

δ (CDCl$_3$, 300 MHz): 0.71 (3H, t), 0.96 (3H, t), 1.46 (4H, m), 1.90 (2H, m), 3.83 (2H, t), 4.12 (2H, s), 4.58 (2H, t), 5.25 (1H, s), 6.86 (1H, s), 7.23 (3H, m), 7.34 (2H, m), 8.48 (1H, s), 8.74 (1H, s), 10.26 (1H, s).

LRMS: m/z 562 (M+1)$^+$.

Preparation 14
5-[2-Ethoxy-5-(4-ethylpiperazin-1-ylsulfonyl)pyridin-3-ylcarboxamido]-2-methyl-1-n-propylimidazole-4-carboxamide (i) Benzotriazol-1-yloxytris(pyrrolidino)phosphonium hexafluorophosphate (304 mg, 0.58 mmol) was added to a solution of pyridine 2-ethoxy-5-(4-ethylpiperazin-1-ylsulfonyl)-3-carboxylic acid (Preparation 12; 200 mg, 0.58 mmol) in N,N-dimethylformamide (3 mL), and the mixture stirred at room temperature for an hour. (ii) 5-Amino-2-methyl-1-n-propylimidazole-4-carboxamide (Preparation 1; 117 mg, 0.64 mmol) was dissolved in hot N,N-dimethylformamide (8 mL), the solution cooled, sodium hydride (22 mg, 60% dispersion in mineral oil, 0.55 mmol) added and the mixture stirred for an hour. The previously prepared solution of activated acid (from (i) above) was then added, followed by sodium hydride (22 mg, 60% dispersion in mineral oil, 0.55 mmol), and the reaction stirred at room temperature for 3 days, and warmed to 60° C. for a further 4 days. The cooled mixture was poured into 2% aqueous sodium bicarbonate solution (30 mL), and extracted with ethyl acetate (2×25 mL). The combined organic extracts were dried (MgSO$_4$), and evaporated under reduced pressure. The residual gum was purified by column chromatography on silica gel, eluting with dichloromethane:methanol (92:8), to give the title compound (39 mg, 13%).

δ (CDCl$_3$, 400 MHz): 0.88 (3H, t), 1.02 (3H, t), 1.58 (3H, t), 1.74 (2H, m), 2.40 (5H, m), 2.55 (4H, m), 3.10 (4H, m), 3.95 (2H, t), 4.78 (2H, q), 5.20 (1H, s), 6.77 (1H, s), 8.68 (1H, s), 8.80 (1H, s), 10.42 (1H, s).

LRMS: m/z 508 (M+1)$^+$.

Preparation 15
9-(4-Nitrophenyl)-2-(2-n-propoxyphenyl)purin-6-one and
Preparation 16
7-(4-Nitrophenyl)-2-(2-n-propoxyphenyl)purin-6-one A mixture of 2-(2-n-propoxyphenyl)-9H-purin-6-one (prepared as described in EP 352 960; 570 mg, 2.11 mmol), cesium carbonate (1.37 g, 4.22 mmol) and 1-nitro-4-fluorobenzene (270 μL, 1.76 mmol) in dimethylsulfoxide (15 mL) was heated under reflux for 3 hours. The cooled reaction was partitioned between water and ethyl acetate, and the resulting precipitate filtered off. The layers of the filtrate were separated, the organic phase dried (MgSO$_4$) and evaporated under reduced pressure. The resulting residue and the filtered solid were combined and purified by column chromatography, eluting with a gradient of dichloromethane:methanol (100:0 to 90:10), to give the title compound of Preparation 15 (244 mg, 35%) as the less polar compound, δ (CDCl$_3$, 300 MHz): 1.20 (3H, t), 2.04 (2H, m), 4.22 (2H, t), 7.10 (1H, d), 7.20 (1H, m), 7.54 (1H, m), 7.84 (2H, d), 8.20 (1H, s), 8.42 (2H, d), 8.74 (1H, d), 11.70 (1H, s).

LRMS: m/z 392 (M+1)$^+$.

followed by the title compound of Preparation 16 (321 mg, 46%) as the more polar compound.

δ (CDCl$_3$, 300 MHz): 1.18 (3H, t), 2.06 (2H, m), 4.25 (2H, t), 7.15 (2H, m), 7.55 (1H, m), 8.04 (2H, d), 8.15 (1H, s), 8.42 (1H, d), 8.50 (2H, d), 11.62 (1H, s).

Preparation 17
8-Benzyl-2-(2-ethoxyphenyl)-9-n-propylpurin-6-one

Potassium bis(trimethylsilyl)amide (81 mg, 0.40 mmol) was added to a solution of 2-benzyl-5-(2-ethoxybenzamido)-1-n-propylimidazole-4-carboxamide (Preparation 3; 110 mg, 0.27 mmol) in ethanol (10 mL), and the reaction heated at 100° C. in a sealed vessel for 18 hours. The cooled mixture was evaporated under reduced pressure, and the residue purified by column chromatography on silica gel, using an elution gradient of dichloromethane:methanol (100:0 to 90:10), to afford the title compound (98 mg, 94%).

δ (CDCl$_3$, 300 MHz): 0.85 (3H, t), 1.64 (5H, m), 3.99 (2H, t), 4.32 (4H, m), 7.02–7.16 (2H, m), 7.28 (5H, m), 7.46 (1H, m), 8.44 (1H, d), 11.30 (1H, s).

LRMS: m/z 389 (M+1)$^+$.

Preparation 18
8-Benzyl-2-(2-n-butoxy-5-iodopyridin-3-yl)-9-n-propylpurin-6-one

The title compound was obtained in 87% yield from 2-benzyl-5-(2-n-butoxy-5-iodopyridin-3-ylcarboxamido)-1-n-propylimidazole-4-carboxamide (Preparation 13), following the procedure described in Preparation 17.

δ (CDCl$_3$, 300 MHz): 0.86 (3H, t), 1.00 (3H, t), 1.54 (2H, m), 1.65 (2H, m), 1.94 (2H, m), 4.00 (2H, t), 4.28 (2H, s), 4.59 (2H, t), 7.28 (5H, m), 8.46 (1H, s), 8.95 (1H, s), 11.08 (1H, s).

LRMS: m/z 544 (M+1)$^+$.

Preparation 19
2-(2-n-Propoxyphenyl)-8-(pyridin-3-yl)-9H-purin-6-one

A mixture of 5,6-diamino-2-(2-propoxyphenyl)-4 (3H)-pyrimidinone (prepared as described in J. Med. Chem. 18, 1117 (1975); 520 mg, 2.0 mmol), 3-pyridinecarboxaldehyde (214 mg, 2.0 mmol) and sodium metabisulfite (494 mg, 2.6 mmol) in N,N-dimethylacetamide (10 mL) was heated under reflux for 20 hours. The cooled mixture was diluted with water (50 mL) and extracted with ethyl acetate (3×40 mL). The combined organic extracts were filtered, the filtrate washed with brine (3×30 mL), dried (MgSO$_4$) and evaporated under reduced pressure. The crude product was purified by column chromatography on silica gel, using an elution gradient of hexane:dichloromethane:methanol (50:50:0 to 0:95:5), to give the title compound as a solid, 172 mg. A sample was recrystallised from ethanol:ethyl acetate.

δ (DMSO-d$_6$, 300 MHz): 1.00 (3H, t), 1.80 (2H, m), 4.10 (2H, t), 7.20 (2H, m), 7.55 (2H, m), 7.80 (1H, m), 8.50 (1H, m), 8.70 (1H, s), 9.35 (1H, s), 11.98 (1H, s), 13.98 (1H, s). m.p. 282–284° C.

Preparation 20
2-(5-Chlorosuphonyl-2-n-propoxyphenyl)-9H-purin-6-one 2-(2-n-Propoxyphenyl)-9H-purin-6-one (prepared as described in EP 352 960; 1.08 g, 4.0 mmol) was added to an ice-cooled solution of thionyl chloride (2 mL, 27.4 mmol), and chlorosulfonic acid (6 mL, 90.2 mmol), and the reaction mixture was allowed to warm slowly to room temperature, and stirred for a further 18 hours. Ice (15 g) was carefully added, the mixture then diluted with water and the resulting precipitate filtered, washed with water, then ether, and dried to give the title compound as white solid (1.27 g, 86%).

δ (DMSO-d$_6$, 300 MHz): 0.98 (3H, t), 1.76 (2H, m), 4.08 (2H, t), 7.15 (1H, d), 7.72 (1H, d), 8.06 (1H, s), 8.80 (1H, s), 9.60–10.08 (1H, br s), 12.14–12.40 (1H, br s).

LRMS: m/z 369 (M+1)$^+$.

Synthesis of the Compounds of Formulae IA and IB

Example 1
2-[5-(4-Ethylpiperazin-1-ylsulfonyl)-2-n-propoxyphenyl]-9H-purin-6-one N-Ethylpiperazine (856 μL, 6.74 mmol) was added to a solution of 2-(5-chlorosuphonyl-2-n-propoxyphenyl)-9H-purin-6-one (Preparation 20; 1.24 g, 3.37 mmol) in ethanol (10 mL), and the reaction stirred at room temperature for 18 hours. The mixture was concentrated under reduced pressure, the residue partitioned between dichloromethane and water, and the layers separated. The aqueous phase was extracted with dichloromethane, the combined organic solutions dried (MgSO$_4$) and evaporated under reduced pressure. The crude product was triturated with ether, the suspension filtered, and the solid dried under vacuum, to give the title compound (1.35 g, 45%).

Anal. Found: C, 52.98; H, 6.44; N, 18.48. C$_{20}$H$_{26}$N$_6$O$_4$S;0.4H$_2$O requires C, 52.94; H, 5.95; N, 18.52%

δ (DMSO-d$_6$, 300 MHz):0.95 (6H, m), 1.78 (2H, m), 2.30 (2H, q), 2.40 (4H, m), 2.89 (4H, m), 4.17 (2H, t), 7.40 (1H, d), 7.82 (1H, d), 7.98 (1H, s), 8.14 (1H, s), 12.00 (1H, br s), 13.20 (1H, br s).

LRMS: m/z 447 (M+1)$^+$.

Example 2
8-Benzyl-2-[2-ethoxy-5-(4-ethylpiperazin-1-ylsulfonyl)phenyl]-9-n-propyl-purin-6-one (i) 8-Benzyl-2-[5-chlorosulfonyl-2-ethoxyphenyl]-9-n-propylpurin-6-one Chlorosulfonic acid (55 μL, 0.82 mmol) was added dropwise to a cooled solution of 8-benzyl-2-(2-ethoxyphenyl)-9-n-propylpurin-6-one (Preparation 17; 160 mg, 0.41 mmol) in dichloromethane (5 mL), and the reaction stirred at room temperature for 18 hours. The mixture was poured onto ice, the phases separated, and the aqueous layer extracted with dichloromethane. The combined organic solutions were evaporated under reduced pressure to afford the sub-title compound (74 mg).

(ii) 8-Benzyl-2-[2-ethoxy-5-(4-ethylpiperazin-1-ylsulfonyl)phenyl]-9-n-propylpurin-6-one N-Ethylpiperazine (73 μL, 0.58 mmol) was added to a solution of 8-benzyl-2-[5-chlorosulfonyl-2-ethoxyphenyl]-9-n-propylpurin-6-one (from (i) above; 70 mg, 0.14 mmol) in ethanol (5 mL), and the reaction was stirred at room temperature for 18 hours. The reaction mixture was concentrated under reduced pressure, the residue partitioned between dichloromethane and sodium bicarbonate solution and the phases separated. The organic layer was dried (MgSO$_4$), and evaporated under reduced pressure. The crude product was purified by column chromatography on silica gel, using an elution gradient of dichloromethane:methanol (100:0 to 95:5), to give the title compound (40 mg, 17%).

δ (CDCl$_3$, 400 MHz): 0.84 (3H, t), 1.00 (3H, t), 1.61 (5H, m), 2.38 (2H, q), 2.50 (4H, m), 3.06 (4H, m), 4.00 (2H, t), 4.28 (2H, s), 4.40 (2H, q), 7.17 (1H, s), 7.26 (5H, m), 7.83 (1H, d), 8.80 (1H, s), 11.01 (1H, br s).

LRMS: m/z 565 (M+1)$^+$.

Example 3
2-[5-(4-Ethylpiperazin-1-ylsulfonyl)-2-n-propoxyphenyl]-9-(4-nitro-phenyl)purin-6-one (i) 2-[5-Chlorosulfonyl-2-n-propoxyphenyl]-9-(4-nitrophenyl)purin-6-one 9-(4-Nitrophenyl)-2-(2-n-propoxyphenyl)purin-6-one (Preparation 15; 320 mg, 0.81 mmol) was dissolved in chlorosulfonic acid (10 mL), and the solution stirred at room temperature for 18 hours. The mixture was poured carefully onto ice/water, and the resulting precipitate filtered, and dried to give the sub-title compound (300 mg).

(ii) 2-[5-(4-Ethylpiperazin-1-ylsulfonyl)-2-n-propoxyphenyl]-9-(4-nitro-phenyl)purin-6-one A mixture of 2-[5-chlorosulfonyl-2-n-propoxyphenyl]-9-(4-nitrophenyl)-purin-6-one (from (i) above; 300 mg, 0.61 mmol), N-ethyldiisopropyl-amine (320 μL, 1.85 mmol), and N-ethylpiperazine (390 μL, 3.1 mmol) in dichloromethane (10 mL), was stirred at room temperature for 18 hours. The solution was washed with water, dried (MgSO$_4$) and concentrated under reduced pressure. The crude product was purified by column chromatography on silica gel, using an elution gradient of dichloromethane:methanol (100:0 to 90:10), to afford the title compound (260 mg, 57%).

δ (CDCl$_3$, 300 MHz): 1.02 (3H, t), 1.20 (3H, t), 2.09 (2H, m), 2.41 (2H, q), 2.55 (4H, m), 3.09 (4H, m), 4.32 (2H, t), 7.21 (1H, d), 7.92 (1H, d), 8.00 (2H, d), 8.18 (1H, s), 8.46 (2H, d), 8.75 (1H, s), 11.20 (1H, s).

LRMS: m/z 568 (M+1)$^+$.

Example 4
9-(4-Aminophenyl)-2-[5-(4-ethylpiperazin-1-ylsulfonyl)-2-n-propoxy-phenyl]purin-6-one A mixture of 2-[5-(4-ethylpiperazin-1-ylsulfonyl)-2-n-propoxyphenyl]-9-(4-nitrophenyl)purin-6-one (Example 3; 100 mg, 0.176 mmol) and Raney® nickel (50 mg) in n-propanol (5 mL) was hydrogenated at 345 kPa (50 psi) and room temperature for 11 hours. The cooled mixture was filtered through Celite®, and the filtrate evaporated under reduced pressure. The crude product was purified by column chromatography on silica gel, using an elution gradient of dichloromethane:methanol (100:0 to 95:5), to provide the title compound (20 mg, 21%).

δ (CDCl$_3$, 300 MHz): 1.01 (3H, t), 1.18 (3H, t), 2.04 (2H, m), 2.38 (2H, q), 2.48 (4H, m), 3.03 (4H, m), 3.90 (2H, s), 4.27 (2H, t), 6.80 (2H, d), 7.18 (1H, d), 7.42 (2H, d), 7.85 (1H, d), 7.99 (1H, s), 8.78 (1H, s), 11.08 (1H, s).

LRMS: m/z 538 (M+1)$^+$.

Example 5
2-[5-(4-Methylpiperazin-1-ylsulfonyl)-2-n-propoxyphenyl]-8-(pyridin-3-yl)-9H-purin-6-one (i) 2-[5-Chlorosulfonyl-2-n-propoxyphenyl]-8-(pyridin-3-yl)-9H-purin-6-one 2-(2-n-Propoxyphenyl)-8-(pyridin-3-yl)-9H-purin-6-one (Preparation 19; 300 mg, 0.59 mmol) was dissolved in thionyl chloride (189 μL, 2.6 mmol) and chlorosulfonic acid (575 μL, 8.6 mmol) and the reaction stirred at room temperature for 18 hours. Water was carefully added, and the mixture evaporated under reduced pressure to give the crude sulfonyl chloride.

(ii) 2-[5-(4-Methylpiperazin-1-ylsulfonyl)-2-n-propoxyphenyl]-8-(pyridin-3-yl)-9H-purin-6-one The residue was suspended in ethanol (2 mL), N-methylpiperazine (653 μL, 5.9 mmol) added, and the solution stirred at room temperature for 18 hours. The mixture was evaporated under reduced pressure, the residue adsorbed onto silica gel, and purified by column chromatography on silica gel, eluting with ethyl acetate:ethanol:0.880 ammonia (70:30:0.3). The product was re-purified by reverse phase column chromatography on polystyrene resin (MCI gel, from the Mitsubishi Kasei Corporation; CHP 20P; 75–100 Tm), using an elution gradient of water:acetonitrile (100:0 to 60:40) to afford the title compound as a white solid (60 mg, 20%).

δ (CDCl$_3$, 400 MHz): 1.00 (3H, t), 1.80 (2H, m), 2.17 (3H, s), 2.39 (4H, m), 2.92 (4H, m), 4.20 (2H, t), 7.40 (1H, d), 7.46 (1H, m), 7.80 (1H, d), 8.18 (1H, s), 8.42 (1H, d), 8.55 (1H, m), 9.30 (1H, s), 11.45–11.60 (1H, br s).

LRMS: m/z 510 (M+1)$^+$.

Example 6
2-[2-Ethoxy-5-(4-ethylpiperazin-1-ylsulfonyl)pyridin-3-yl]-8-methyl-9-n-propylpurin-6-one A mixture of 5-[2-ethoxy-5-(4-ethylpiperazin-1-ylsulfonyl)pyridin-3-ylcarboxamido)-2-methyl-1-n-propylimidazole-4-carboxamide (Preparation 14; 39 mg, 0.077 mmol) and potassium bis(trimethylsilyl)amide (30.7 mg, 0.15 mmol) in ethanol (6 mL) was heated at 130° C. in a sealed vessel for 15 hours. The cooled mixture was concentrated under reduced pressure to a volume of 1 mL, and then diluted with aqueous sodium bicarbonate solution (15 mL). This was extracted with ethyl acetate (3×15 mL), the combined organic extracts dried (MgSO$_4$), and evaporated under reduced pressure. The residual gum was purified by column chromatography on silica gel, using dichloromethane:methanol (95:5) as eluant, to give the title compound (25 mg, 65%).

δ (CDCl$_3$, 300 MHz): 0.94–1.05 (6H, m), 1.59 (3H, t), 1.85 (2H, m), 2.41 (2H, q), 2.58 (7H, m), 3.15 (4H, m), 4.17 (2H, t), 4.79 (2H, q), 8.64 (1H, s), 9.04 (1H, s), 11.00 (1H, s).

LRMS: m/z 490 (M+1)$^+$.

Example 7
8-Benzyl-2-[2-n-butoxy-5-(4-ethylpiperazin-1-ylsulfonyl)pyridin-3-yl]-9-n-propylpurin-6-one (i) 8-Benzyl-2-[2-n-butoxy-5-sulfanylpyridin-3-yl]-9-n-propylpurin-6-one A mixture of freshly dried thiourea (78 mg, 1.03 mmol) and 8-benzyl-2-(2-n-butoxy-5-iodopyridin-3-yl)-9-n-propylpurin-6-one (Preparation 18; 370 mg, 0.68 mmol) in dry N,N-dimethylformamide (2.75 mL) was warmed to 60° C. before bis(triethylphosphine)nickel(II) chloride (25 mg, 0.068 mmol) and sodium cyanoborohydride (6.3 mg, 0.1 mmol) were added, and the reaction stirred for 30 minutes. Additional nickel catalyst (175 mg, 0.47 mmol) and sodium cyanoborohydride (44.1 mg, 0.7 mmol) were added and the reaction continued for an hour, then removed from the heat. Calcium oxide (55 mg, 0.98 mmol) was added, the reaction stirred for an hour at room temperature and then quenched using 1 N hydrochloric acid. The reaction mixture was partitioned between ethyl acetate and water, and the phases separated. The organic layer was washed with brine and 1 N hydrochloric acid, dried (MgSO$_4$) and evaporated under reduced pressure.

(ii) 8-Benzyl-2-[2-n-butoxy-5-chlorosulfonylpyridin-3-yl]-9-n-propylpurin-6-one

Potassium nitrate (172 mg, 1.7 mmol) was added to a solution of 8-benzyl-2-[2-n-butoxy-5-sulfanylpyridin-3-yl]-9-n-propylpurin-6-one (from (i) above) in acetonitrile (5 mL), and the solution cooled in an ice-bath. Thionyl chloride (140 μL, 1.92 mmol) was added dropwise, and the reaction stirred at room temperature for 3 hours. The mixture was concentrated under reduced pressure, and the residue partitioned between sodium bicarbonate solution and dichloromethane. The layers were separated, and the aqueous layer was extracted with dichloromethane. The combined organic solutions were then washed with brine, dried (MgSO$_4$) and evaporated under reduced pressure.

(iii) 8-Benzyl-2-[2-n-butoxy-5-(4-ethylpiperazin-1-ylsulfonyl)pyridin-3-yl]-9-n-propylpurin-6-one 8-Benzyl-2-[2-n-butoxy-5-chlorosulfonylpyridin-3-yl]-9-n-propylpurin-6-one (the solid resulting from part (ii) above) was dissolved in dichloromethane (5 mL), N-ethyldiisopropylamine (600 μL, 3.47 mmol) and N-ethylpiperazine (430 μL, 3.38 mmol) were added, and the reaction stirred at room temperature for 18 hours. The mixture was concentrated under reduced pressure, and the residue purified by column chromatography on silica gel, using an elution gradient of dichloromethane:methanol (100:0 to 95:5), to afford the title compound (40 mg, 10%).

δ (CDCl$_3$, 300 MHz): 0.83 (3H, t), 1.00 (6H, m), 1.46–1.70 (4H, m), 1.96 (2H, m), 2.40 (2H, q), 2.54 (4H, m), 3.09 (4H, m), 4.00 (2H, t), 4.28 (2H, s), 4.68 (2H, t), 7.26 (5H, m), 8.62 (1H, s), 8.99 (1H, s), 10.98 (1H, s).

LRMS: m/z 594 (M+1)$^+$.

Example 8
2-(2-n-Propoxy-5-[4-{pyridin-2-yl}piperazin-1-ylsulfonyl]phenyl)-9H-purin-6-one (i) 2-(5-Chlorosulfonyl-2-n-propoxyphenyl)-9H-purin-6-one 2-(2-n-Propoxyphenyl)-9H-purin-6-one (prepared as described in EP 352 960; 1.0 g, 3.69 mmol) was dissolved in ice-cold chlorosulfonic acid (5 mL), and the solution stirred at room temperature for 2 hours. The reaction was cautiously poured onto ice, the resulting precipitate filtered off, washed with ethyl acetate and ether, and dried under vacuum, to give a solid, 1.0 g.

(ii) 2-(2-n-Propoxy-5-[4-{pyridin-2-yl}piperazin-1-ylsulfonyl]phenyl)-9H-purin-6-one 2-(5-Chlorosulfonyl-2-n-propoxyphenyl)-9H-purin-6-one (from (i) above; 250 mg) was added to an ice-cold solution of 1-(2-pyridyl)piperazine (294 mg, 1.8 mmol) in ethyl acetate (30 mL), and the reaction then allowed to warm to room temperature, and stirred for a further 6 hours. The reaction mixture was concentrated under reduced pressure, and the residue triturated with a methanol/water mixture (50:50). The resulting solid was filtered, washed with water and ether, and then recrystallised from methanol to afford the title compound as colourless crystals, 207 mg.

m.p. 186.5–187.5° C.

δ (DMSO-$d_6$, 300 MHz): 0.95 (3H, t), 1.75 (2H, m), 2.99 (4H, m), 3.60 (4H, m), 4.15 (2H, t), 6.65 (1H, m), 6.80 (1H, d), 7.40 (1H, d), 7.50 (1H, m), 7.85 (1H, d), 8.00 (1H, s), 8.10 (1H, m), 8.20 (1H, s), 12.05 (1H, br s), 13.40 (1H, br s).

Example 9
2-(2-n-Propoxy-5-[4-{pyridin-2-yl}piperazin-1-ylsulfonyl]phenyl)-9-n-propylpurin-6-one Sodium hydride (41 mg, 60% dispersion in mineral oil, 1.03 mmol) was added to a suspension of 2-(2-n-propoxy-5-[4-{pyridin-2-yl}piperazin-1-ylsulfonyl]phenyl)-9H-purin-6-one (Example 8; 230 mg, 0.45 mmol) in tetrahydrofuran (8 mL), and the mixture stirred at room temperature under a nitrogen atmosphere for 3 hours. 1-Iodopropane (54 μL, 0.54 mmol) was added, and the reaction stirred for 18 hours at room temperature, followed by a further 12 hours at 60° C. The cooled mixture was poured into water, and extracted with ethyl acetate. The combined organic extracts were evaporated under reduced pressure and the crude product purified by column chromatography on silica gel, eluting with dichloromethane:methanol (97:3), to afford the title compound (70 mg, 64%).

Anal. Found: C, 57.31; H, 5.90; N, 17.69. $C_{26}H_{31}N_7O_4S$;0.5$H_2O$ requires C, 57.13; H, 5.90; N, 17.94%.

δ (DMSO-$d_6$, 300 MHz): 0.83 (3H, t), 0.92 (3H, t), 1.70 (2H, m), 1.80 (2H, m), 3.28 (4H, m), 3.59 (4H, m), 4.10 (2H, t), 4.16 (2H, t), 6.61 (1H, m), 6.80 (1H, d), 7.38 (1H, d), 7.50 (1H, m), 7.84 (1H, d), 7.94 (1H, s), 8.04 (1H, m), 8.12 (1H, s), 12.10 (1H, s).

LRMS: m/z 538 (M+1)$^+$.

Example 10
2-[5-(4-Ethylpiperazin-1-ylsulfonyl)-2-n-propoxyphenyl]-7-n-propylpurin-6-one Potassium hydroxide (27.6 mg, 0.49 mmol) was added to a solution of 2-[5-(4-ethylpiperazin-1-ylsulfonyl)-2-n-propoxyphenyl]-9H-purin-6-one (Example 1; 200 mg, 0.45 mmol) in N,N-dimethylformamide (5 mL), and the mixture stirred at room temperature for 4 hours, then cooled in an ice-bath. 1-Iodopropane (76.1 mg, 0.45 mmol) was added, the reaction stirred at 5° C. for 3 hours, and then for a further 18 hours at room temperature. The reaction mixture was concentrated under reduced pressure, the residue suspended in water, and extracted with dichloromethane (×2). The combined organic extracts were dried (MgSO$_4$) and evaporated under reduced pressure. The crude product was purified by column chromatography on silica gel, using an elution gradient of dichloromethane:methanol (98:2 to 96:4), and azeotroped with dichloromethane, to afford the title compound as a white solid (70 mg, 32%).

δ (CDCl$_3$, 300 MHz): 1.00 (6H, m), 1.20 (3H, t), 1.94–2.12 (4H, m), 2.40 (2H, m), 2.54 (4H, m), 3.10 (4H, m), 4.26 (2H, t), 4.38 (2H, t), 7.17 (1H, d), 7.84 (2H, m), 9.03 (1H, s), 11.12 (1H, s).

LRMS: m/z489 (M+1)$^+$.

Example 11
2-[5-(4-Ethylpiperazin-1-ylsulfonyl)-2-n-propoxyphenyl]-7-(4-nitro-phenyl)purin-6-one The title compound was obtained in 60% yield from 7-(4-nitrophenyl)-2-(2-n-propoxyphenyl)purin-6-one (Preparation 16) and N-ethylpiperazine, following the procedure described in Example 3.

δ (CDCl$_3$, 300 MHz): 1.02 (3H, t), 1.20 (3H, t), 2.07 (2H, m), 2.40 (2H, q), 2.57 (4H, m), 3.13 (4H, m), 4.32 (2H, t), 7.20 (1H, d), 7.88 (3H, m), 8.22 (1H, s), 8.42 (2H, d), 9.04 (1H, s), 11.40 (1H, s).

LRMS: m/z 568 (M+1)$^+$.

Example 12
7-(4-Aminophenyl)-2-[5-(4-ethylpiperazin-1-ylsulfonyl)-2-n-propoxy-phenyl]purin-6-one Iron powder (137 mg, 2.45 mmol) was added to a solution of 2-[5-(4-ethylpiperazin-1-ylsulfonyl)-2-n-propoxyphenyl]-7-(4-nitrophenyl)purin-6-one (Example 11; 110 mg, 0.19 mmol) in acetic acid (2.2 mL) and water (100 μL), and the reaction stirred vigorously at room temperature for 3 hours. The mixture was filtered through Celite®, washing well with ethyl acetate, and the filtrate concentrated under reduced pressure. The residue was partitioned between ethyl acetate and sodium bicarbonate solution, the layers separated, and the organic phase dried (MgSO$_4$) and evaporated under reduced pressure to give the title compound (80 mg, 79%).

δ (CDCl$_3$, 300 MHz): 1.06–1.24 (6H, m), 2.03 (2H, m), 2.50–2.80 (6H, m), 3.21 (4H, m), 3.90 (2H, s), 4.26 (2H, t), 6.78 (2H, d), 7.18 (1H, d), 7.35 (2H, d), 7.86 (1H, d), 8.03 (1H, s), 9.05 (1H, s), 11.21 (1H, s).

LRMS: m/z 538 (M+1)$^+$.

Biological Activity

Compounds of the invention were found to have in vitro activities as 30 inhibitors of cGMP PDE5 with IC$_{50}$ values of less than about 100 nM.

The following Table illustrates the in vitro activities for a range of compounds of the invention as inhibitors of CGMP PDE5.

| Example number | Concentration (nM) | Percentage inhibition of PDE 5 |
|---|---|---|
| 1 | 100 | 47 |
| 4 | 10 | 74.1 |
| 5 | 100 | 48 |
| 7 | 10 | 80.3 |
| 9 | 10 | 100 |

Abbreviations
The following abbreviations may be used herein:

| | |
|---|---|
| Ac = | acetyl |
| aq. = | aqueous |
| br = | broad (in relation to NMR) |
| d = | doublet (in relation to NMR) |
| DCM = | dichloromethane |
| dd = | doublet of doublets (in relation to NMR) |
| DMF = | N,N-dimethylformamide |

-continued

| | |
|---|---|
| DMSO = | dimethylsulfoxide |
| Et = | ethyl |
| EtOAc = | ethyl acetate |
| h = | hour(s) |
| HPLC = | high performance liquid chromatography |
| IMS = | industrial methylated spirits |
| IPA = | iso-propyl alcohol (propan-2-ol) |
| LRMS = | low resolution mass spectrometry |
| m = | multiplet (in relation to NMR) |
| Me = | methyl |
| MeCN = | acetonitrile |
| MeOH = | methanol |
| min. = | minute(s) |
| m.p. = | melting point |
| MS = | mass spectroscopy |
| OAc = | acetate |
| q = | quartet (in relation to NMR) |
| rt = | room temperature |
| s = | singlet (in relation to NMR) |
| t = | triplet (in relation to NMR) |
| THF = | tetrahydrofuran |

What is claimed is:
1. A compound of formula IB,

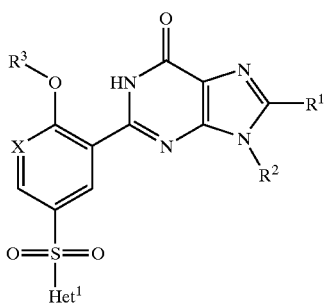

wherein

X represents N;

$R^1$ represents H, —CN, —C(O)N($R^4$)$R^5$, —C(O)$R^4$, —C(O)O$R^4$, —N($R^4$)$R^6$, —O$R^7$, aryl, Het$^2$ or lower alkyl optionally interrupted by one or more of —O—, —S— or —N($R^4$)— and/or substituted and/or terminated by one or more substituents selected from the group consisting of halo, —CN, —NO$_2$, lower alkyl, —C(O)N($R^4$)$R^5$, —C(O)$R^4$, —C(O)O$R^4$, —N($R^4$)$R^6$, —O$R^7$, —S(O)$_n$$R^4$, —S(O)$_2$N($R^4$)$R^5$, aryl and Het$^2$;

$R^6$ represents $R^5$, —S(O)$_2$$R^8$, —S(O)$_2$N($R^4$)$R^5$, —C(O)$R^4$, —C(O)O$R^8$ or —C(O)N($R^4$)$R^5$;

$R^7$ represents $R^4$ or —C(O)$R^4$;

$R^3$, $R^4$, $R^5$ and $R^8$ independently represent, at each occurrence, lower alkyl optionally substituted and/or terminated by one or more substituents selected from the group consisting of lower alkyl, aryl, Het$^3$, halo, —CN, —NO$_2$, —OR$^{9a}$, —C(O)R$^{9b}$, —C(O)OR$^{9c}$, —C(O)N(R$^{9d}$)R$^{9e}$, —S(O)$_2$R$^{10a}$, —S(O)$_2$N(R$^{9f}$)R$^{9g}$, —OC(O)R$^{9h}$ and —N(R$^{11}$)R$^{9i}$;

$R^3$, $R^4$ and $R^5$ may also, at each occurrence, independently represent H;

$R^4$, $R^5$ and $R^8$ may also, at each occurrence, independently represent aryl;

$R^2$ represents H, aryl, Het$^4$ or lower alkyl optionally substituted by one or more substituents selected from the group consisting of lower alkyl optionally substituted by one or more substituents selected from —OH or halo, aryl, Het$^5$, halo, —CN, —NO$_2$, —OR$^{9a}$, —C(O)R$^{9b}$, —C(O)OR$^{9c}$, —C(O)N(R$^{9d}$)R$^{9e}$, —S(O)$_2$R$^{10a}$, —S(O)$_2$N(R$^{9f}$)R$^{9g}$, —OC(O)R$^{9h}$ and —N(R$^{11}$)R$^{9i}$;

$R^{11}$ represents, at each occurrence, H, aryl, lower alkyl optionally substituted by one or more substituents selected from the group consisting of aryl and halo, —C(O)R$^{9j}$, —C(O)N(R$^{9k}$)R$^{9m}$ or —S(O)$_2$R$^{10b}$;

$R^{9a}$ to $R^{9m}$ independently represent, at each occurrence, H, aryl or lower alkyl optionally substituted by one or more substituents selected from the group consisting of aryl and halo;

$R^{10a}$ and $R^{10b}$ represent, at each occurrence, aryl or lower alkyl optionally substituted by one or more substituents selected from the group consisting of aryl and halo;

Het$^1$ represents an optionally substituted four- to twelve-membered heterocyclic group, which group contains at least one nitrogen atom by which the Het$^1$ group is attached to the compound and, optionally, one or more further heteroatoms selected from the group consisting of nitrogen, oxygen and sulfur;

Het$^2$ to Het$^5$ independently represent optionally substituted four- to twelve-membered heterocyclic groups, which groups contain one or more heteroatoms selected from the group consisting of nitrogen, oxygen and sulfur;

each aryl group is optionally substituted with one or more substituents selected from the group consisting of halo, lower alkyl optionally substituted by one or more substituents selected from —CN, —NO$_2$, —OR$^{9a}$, —C(O)R$^{9b}$, —C(O)OR$^{9c}$, —C(O)N(R$^{9d}$)R$^{9e}$, —S(O)$_2$N(R$^{9f}$)R$^{9g}$, —S(O)$_n$R$^{10a}$, —OC(O)R$^{9h}$ or —N(R$^{11}$)R$^{9i}$), —CN, —NO$_2$, —OR$^{9a}$, —C(O)R$^{9b}$, —C(O)OR$^{9c}$, —C(O)N(R$^{9d}$)R$^{9e}$, —S(O)$_n$R$^{10a}$, —S(O)$_2$N(R$^{9f}$)R$^{9g}$, —OC(O)R$^{9h}$ and —N(R$^{11}$)R$^{9i}$;

Het$^1$, Het$^2$, Het$^3$, Het$^4$ and Het$^5$ are each optionally substituted with one or more substituents selected from the group consisting of lower alkyl optionally substituted by one or more substituents selected from lower alkyl, aryl, Het$^2$, halo, —CN, —NO$_2$, —OR$^{9a}$, —C(O)R$^{9b}$, —C(O)OR$^{9c}$, —C(O)N(R$^{9d}$)R$^{9e}$, —S(O)$_n$R$^{10a}$, —S(O)$_2$N(R$^{9f}$)R$^{9g}$, —OC(O)R$^{9h}$ or —N(R$^{11}$)R$^{9i}$), aryl, Het$^2$, halo, —CN, —NO$_2$, —OR$^{9a}$, —C(O)R$^{9b}$, —C(O)OR$^{9c}$, —C(O)N(R$^{9d}$)R$^{9e}$, —S(O)$_n$R$^{10a}$, —S(O)$_2$ N(R$^{9f}$)R$^{9g}$, —OC(O)R$^{9h}$ and —N(R$^{11}$)R$^{9i}$; and n represents, at each occurrence, 0, 1 or 2;

or a pharmaceutically or veterinarily acceptable salt, solvate or prodrug thereof.

2. A compound as defined in claim 1 wherein at least one of the following applies:

(1) $R^1$ represents —CN, —C(O)N($R^4$)$R^5$, —C(O)$R^4$, —C(O)O$R^4$, —N($R^4$)$R^6$, —O$R^7$, aryl, Het$^2$ or lower alkyl optionally interrupted by one or more of —O—, —S— or —N($R^4$)— substituted by one or more substituents selected from the group consisting of halo, —CN, —NO$_2$, lower alkyl, —C(O)N($R^4$)$R^5$, —C(O)$R^4$, —C(O)O$R^4$, —N($R^4$)$R^6$, —O$R^7$, —S(O)$_n$$R^4$ or —S(O)$_n$N($R^4$)$R^5$, aryl and Het$^2$;

(2) $R^2$ represents H, aryl, Het$^4$, $C_{1-2}$ alkyl substituted by one or more substituents selected from the group consisting of aryl, —OR$^{9a}$, —C(O)R$^{9b}$, —OC(O)R$^{9h}$ and —N(R$^{11}$)R$^{9i}$ or lower alkyl substituted by:

(i) one or more substituents selected from the group consisting of halo, —CN, —NO$_2$, Het$^5$, —OR$^{9a}$, —C(O)R$^{9b}$ wherein R$^{9a}$ and R$^{9b}$ represent aryl or lower alkyl substituted by one or more halo atoms —C(O)OR$^{9c}$, —C(O)N(R$^{9d}$)R$^{9e}$, —S(O)$_2$R$^{10a}$, —S(O)$_2$N(R$^{9f}$)R$^{9g}$ and —N(R$^{11}$)R$^{9i}$ wherein R$^{11}$ represents aryl or —C(O)N(R$^{9k}$)R$^{9m}$); or (ii) more than one substituent selected from the group consisting of —OR$^{9a}$ wherein R$^{9a}$ represents aryl or lower alkyl optionally substituted by one or more substituents selected from aryl or halo, —C(O)R$^{9b}$, —CO(O)R$^{9h}$ and —N(R$^{11}$)R$^{9i}$;

(3) R$^3$ represents H or lower alkyl substituted by one or more substituents selected from the group consisting of aryl, Het$^3$, halo, —CN, —NO$_2$, —OR$^{9a}$, —C(O)R$^{9b}$, —C(O)OR$^{9c}$, —C(O)N(R$^{9d}$)R$^{9e}$, —S(O)$_2$R$^{10a}$, —S(O)$_2$ N(R$^{9f}$)R$^{9g}$, —OC(O)R$^{9h}$ and —N(R$^{11}$)R$^{9i}$; or (4) Het$^1$ represents:
  (i) a 4- or 7- to 12-membered optionally substituted heterocyclic group as defined in claim 1;
  (ii) a 5- or 6-membered fully saturated heterocyclic group as defined in claim 1, which group is not substituted by C$_{1-6}$ alkyl optionally substituted by —OH; or
  (iii) a 5- or 6-membered optionally substituted, partly unsaturated or aromatic heterocyclic group as defined in claim 1;
wherein, unless otherwise specified, substituents n, R$^4$, R$^5$, R$^6$, R$^7$, R$^{9a}$ to R$^{9m}$, R$^{10a}$, R$^{11}$, Het$^2$, Het$^4$ and Het$^5$ are as defined in claim 1.

3. A compound as defined in claim 1 wherein at least one of the following applies:

(1) R$^1$ represents —CN, —C(O)N(R$^4$)R$^5$, —C(O)R$^4$, —C(O)OR$^4$, —N(R$^4$)R$^6$, —OR$^7$, aryl, Het$^2$ or lower alkyl optionally interrupted by one or more of —O—, —S— or —N(R$^4$)— or substituted by one or more substituents selected from the group consisting of halo, —CN, —NO$_2$, lower alkyl, —C(O)N(R$^4$)R$^5$, —C(O)R$^4$, —C(O)OR$^4$, —N(R$^4$)R$^6$, —OR$^7$, —S(O)$_n$R$^4$, —S(O)$_n$N(R$^4$)R$^5$, aryl and Het$^2$;

(2) R$^2$ represents H, aryl, Het$^4$, C$_{1-2}$ alkyl substituted by one or more substituents selected from the group consisting of aryl, —OR$^{9a}$, —C(O)R$^{9b}$, —OC(O)R$^{9h}$ and —N(R$^{11}$)R$^{9i}$), or lower alkyl substituted by:
  (i) one or more substituents selected from the group consisting of halo, —CN, —NO$_2$, Het$^5$, —OR$^{9a}$, —C(O)R$^{9b}$ wherein R$^{9a}$ and R$^{9b}$ represent aryl or lower alkyl substituted by one or more halo atoms, —C(O)OR$^{9c}$, —C(O)N(R$^{9d}$)R$^{9e}$, —S(O)$_2$R$^{10a}$, —S(O)$_2$N(R$^{9f}$)R$^{9g}$ and —N(R$^{11}$)R$^{9i}$ wherein R$^{11}$ represents aryl or —C(O)N(R$^{9k}$)R$^{9m}$); or
  (ii) more than one substituent selected from the group consisting of —OR$^{9a}$ wherein R$^{9a}$ represents aryl or lower alkyl optionally substituted by one or more substituents selected from aryl or halo, —C(O)R$^{9b}$, —OC(O)R$^{9h}$ and —N(R$^{11}$)R$^{9i}$;

(3) R$^3$ represents H or lower alkyl substituted by one or more substituents selected from the group consisting of aryl, Het$^3$, halo, —CN, —NO$_2$, —OR$^{9a}$, —C(O)R$^{9b}$, —C(O)OR$^{9c}$, —C(O)N(R$^{9d}$)R$^{9e}$, —S(O)$_2$R$^{10a}$, —S(O)$_2$ N(R$^{9f}$)R$^{9g}$, —OC(O)R$^{9h}$, and —N(R$^{11}$)R$^{9i}$; or (4) Het$^1$ represents:
  (i) a 4- or 7- to 12-membered optionally substituted heterocyclic group as defined in claim 1;
  (ii) a 5- or 6-membered fully saturated heterocyclic group as defined in claim 1, which group is not substituted by C$_{1-6}$ alkyl optionally substituted by —OH; or
  (iii) a 5- or 6-membered optionally substituted, partly unsaturated or aromatic heterocyclic group as defined in claim 1;

wherein, unless otherwise specified, substituents n, R$^4$, R$^5$, R$^6$, R$^7$, R$^{9a}$ to R$^{9m}$, R$^{10a}$, R$^{11}$, Het$^2$, Het$^4$ and Het$^5$ are as defined in claim 1.

4. A compound of claim 1, wherein R$^1$ represents H, —CN, —C(O)N(R$^4$)R$^5$, —C(O)R$^4$, —C(O)OR$^4$, —N(R$^4$) R$^6$, —OR$^7$, aryl, Het$^2$ or C$_{1-6}$ alkyl optionally substituted by one or more substituents selected from the group consisting of halo, —CN, —NO$_2$, lower alkyl, —C(O)N(R$^4$)R$^5$, —C(O)R$^4$, —C(O)OR$^4$, —N(R$^4$)R$^6$, —OR$^7$, —S(O)$_n$R$^4$, —S(O)$_n$N(R$^4$)R$^5$, aryl and Het$^2$.

5. A compound of claim 1 wherein R$^6$ represents R$^5$, —S(O)$_2$R$^8$ or —C(O)R$^4$.

6. A compound of claim 1 wherein R$^7$ represents R$^4$.

7. A compound of claim 1 wherein R$^3$, R$^4$, R$^5$ and R$^8$ independently represent lower alkyl optionally substituted by one or more substituents selected from the group consisting of aryl, Het$^3$, halo, —CN, —NO$_2$, —OR$^{9a}$, and —N(R$^{11}$)R$^{9i}$; R$^3$, R$^4$ and R$^5$ independently represent H; or R$^4$, R$^5$ and R$^8$ independently represent aryl.

8. A compound of claim 1 wherein R$^2$ represents H, aryl, Het$^4$ or lower alkyl optionally substituted by one or more substituents selected from halo, —CN, —NO$_2$, aryl, Het$^5$, —OR$^{9a}$, —C(O)R$^{9b}$, —C(O)OR$^{9c}$, —C(O)N(R$^{9d}$)R$^{9e}$, —S(O)$_n$R$^{10a}$, —S(O)$_2$N(R$^{9f}$)R$^{9g}$ or —N(R$^{11}$)R$^{9i}$.

9. A compound of claim 1 wherein n represents 0 or 2.

10. A compound of claim 1 wherein R$^{11}$ represents H, C$_{1-6}$ alkyl or —C(O)R$^{9j}$.

11. A compound of claim 1 wherein R$^{9a}$ to R$^{9j}$ independently represent H or C$_{1-6}$ alkyl.

12. A compound of claim 1 wherein R$^{10a}$ represents C$_{1-6}$ alkyl.

13. A compound of claim 1 wherein Het$^1$ represents a four- to seven-membered heterocyclic group, which group contains at least one nitrogen atom by which the Het$^1$ group is attached to the rest of the compound and, optionally, one or more further heteroatoms selected from the group consisting of nitrogen and oxygen, and is optionally substituted as defined in claim 1.

14. A compound of claim 1 wherein Het$^2$ to Het$^5$ independently represent four- to ten-membered heterocyclic groups containing between one and four heteroatoms selected from the group consisting of nitrogen, oxygen and sulfur, and which groups are optionally substituted as defined in claim 1.

15. A pharmaceutical formulation comprising a compound of claim 1 and a pharmaceutically acceptable adjuvant, diluent or carrier.

16. A veterinary formulation comprising a compound of claim 1 and a veterinarily acceptable adjuvant, diluent or carrier.

17. A method of treating or preventing a medical condition for which inhibition of cGMP PDE5 is desired, which comprises administering a therapeutically effective amount of a compound of claim 1 to a patient in need of such treatment.

18. The method of claim 17, wherein the condition is male erectile dysfunction, impotence, female sexual dysfunction, clitoral dysfunction, female hypoactive sexual desire disorder, female sexual arousal disorder, female sexual pain disorder or female sexual orgasmic dysfunction.

19. The method of claim 17, wherein the condition is male erectile dysfunction.

* * * * *